US006420397B1

(12) United States Patent
Pan et al.

(10) Patent No.: US 6,420,397 B1
(45) Date of Patent: Jul. 16, 2002

(54) HETEROARYL PROTEASE INHIBITORS AND DIAGNOSTIC IMAGING AGENTS

(75) Inventors: Wenxi Pan, Exton; Tianbao Lu, Collegeville, both of PA (US); Richard M. Soll, Lawrenceville, NJ (US); Bruce E. Tomczuk, Collegeville, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/612,591

(22) Filed: Jul. 7, 2000

Related U.S. Application Data

(60) Provisional application No. 60/142,929, filed on Jul. 9, 1999.

(51) Int. Cl.[7] .................. A61K 31/4412; A61K 31/425; C07D 417/00
(52) U.S. Cl. ................... 514/352; 514/357; 514/365; 514/374; 546/268.2; 546/269.7; 546/271.4
(58) Field of Search .................... 546/268.2, 269.7, 546/271.4; 514/352, 357, 365, 374

(56) References Cited

U.S. PATENT DOCUMENTS

| 4,418,052 A | 11/1983 | Wong ........................... 424/1.1 |
| 4,652,440 A | 3/1987 | Paik et al. .................... 424/1.1 |
| 4,727,064 A | 2/1988 | Pitha ............................ 514/58 |
| 4,764,604 A | 8/1988 | Müller ........................ 536/103 |
| 4,957,939 A | 9/1990 | Greis et al. ................. 514/492 |
| 4,980,148 A | 12/1990 | Dean ............................. 424/9 |
| 5,011,686 A | 4/1991 | Pang .......................... 424/94.1 |
| 5,024,829 A | 6/1991 | Berger et al. ................. 424/1.1 |
| 5,024,998 A | 6/1991 | Bodor .......................... 514/58 |
| 5,122,361 A | 6/1992 | Kung et al. .................. 424/1.1 |
| 5,466,811 A | 11/1995 | Alexander ................... 546/283 |
| 5,656,600 A | 8/1997 | Abelman et al. ............. 514/13 |
| 5,792,779 A | * 8/1998 | Sandoerson et al. ........ 514/352 |
| 5,891,909 A | 4/1999 | Soll et al. ................... 514/517 |

FOREIGN PATENT DOCUMENTS

| CA | 2164684 | 6/1996 |
| EP | 0 363 284 A2 | 4/1990 |
| EP | 0 604 022 A1 | 6/1994 |
| EP | 0 761 251 A1 | 3/1997 |
| WO | WO 95/07291 | 3/1995 |
| WO | WO 96/11668 | 4/1996 |
| WO | WO 96/18644 | 6/1996 |
| WO | WO 96/32143 | 10/1996 |
| WO | WO 96/38136 | 12/1996 |
| WO | WO 97/01338 | 1/1997 |
| WO | WO 97/30708 | 8/1997 |
| WO | 9816547 | * 4/1998 |
| WO | WO 99/26926 | 6/1999 |
| WO | 9926926 | * 6/1999 |

OTHER PUBLICATIONS

International Search Report for International Application No. PCT/US00/40332, mailed Dec. 7, 2000.

Barrett, A.J., "Proteinase inhibitors: potential drugs?" in *Enzyme Inhibitors as Drugs*, Sandler, M., ed., The MacMillan Press Ltd., London, England, pp.219–229 (1980).

Baugh, R.J. and Travis, J., "Human Leukocyte Granule Elastase: Rapid Isolation and Characterization," *Biochemistry* 15:836–841 American Chemical Society, Washington DC (1976).

Brown, F.J. er al., "Design of Orally Active, non–Peptidic Inhibitors of Human Leukocyte Elastase," *J. Med. Chem.* 37:1259–1262 American Chemical Society, Washington, DC (1994).

(List continued on next page.)

*Primary Examiner*—Mukund J. Shah
*Assistant Examiner*—Sudhaker B Patel
(74) *Attorney, Agent, or Firm*—Sterne, Kessler, Goldstein & Fox P.L.L.C.

(57) ABSTRACT

Ketothiazole alkoxyguanidine and aminoguanidine analogs are described, including compounds of the Formula I:

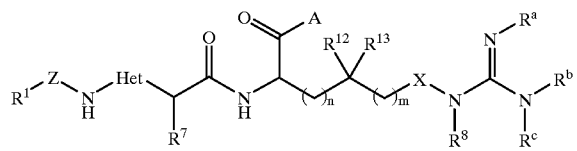

wherein X is O or $NR^9$ and Het, A, $R^1$, $R^7$, $R^8$, $R^{12}$, $R^{13}$, $R^a$, $R^b$, $R^c$, Z, m and n are set forth in the specification, as well as hydrates, solvates or pharmaceutically acceptable salts thereof, that inhibit proteolytic enzymes such as thrombin. Also described are methods for preparing such compounds. The compounds of the invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin. The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

35 Claims, No Drawings

OTHER PUBLICATIONS

Claeson, G., "Synthetic peptides and peptidomimetics as substrates and inhibitors of thrombin and other proteases in the blood coagulation system," *Blood Coagulation and Fibrinolysis* 5:411–436 Rapid Communications of Oxford Ltd., New York, NY (1994).

Coughlin, S.R., "Molecular Mechanisms of Thrombin Signaling," *Seminars in Hematology* 31:270–277 W.B. Saunders, Co., Philadelphia, PA (1994).

Cuypers, H.T. et al., "Sulfhydryl Content of Bovine Eye Lens Leucine Aminopeptidase. Determination of the Reactivity of the Sulfhydryl Groups of the Zinc Metalloenzyme, of the Enzyme Activated by $Mg^{2+}$, $Mn^{2+}$, and $Co^{2+}$, and of the Metal–Free Apoenzyme," *J. Biol. Chem.* 257:7086–7091 American Society for Biochemistry and Molecular Biology, Inc., Bethesda, MD (1982).

de Roos, A. et al., "Myocardial infarct sizing and assessment of reperfusion by magnetic resonance imaging: a review," *Int. J. Cardiac Imaging* 7:133–138 Kluwer Academic Publishers, Dordrecht, Netherlands (1991).

Edwards, P.D. et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole," *J. Am. Chem. Soc.* 114:1854–1863 American Chemical Society, Washington, DC (1992).

Harker, L.A., "Strategies for inhibiting the effects of thrombin," *Blood Coagulation and Fibrinolysis* 5:S47–S58 Rapid Communications of Oxford Ltd., New York, NY (1994).

Jeong, J.–H. et al., "Cyclic Guanidino–Sugars with Low $pK_a$ as Transition–State Analog Inhibitors of Glycosidases: Neutral Instead of Charged Species Are the Active Forms," *J. Am. Chem. Soc.* 118:4227–4234 American Chemical Society, Washington, DC (1996).

Khaw, B.A. et al., "Myocardial Infarct Imaging of Antibodies to Canine Cardiac Myosin wih Indium–111–Diethylenetriamine Pentaacetic Acid," *Science* 209:295–297 American Academy for the Advancement of Sciences, Washington, DC (1980).

Kim, K.S. et al., "Preparation of Argatroban Analog Thrombin Inhibitors with Reduced Basic Guanidine Moiety, and Studies of Their Cell Permeability and Antithrombotic Activites," *Med. Chem. Res.* 6:377–383 Birkhäuser Press, Boston, MA (1996).

Lefkovits, J., and Topol, E.J., "Direct Thrombin Inhibitors in Cardiovascular Medicine," *Circulation* 90:1522–1536 Lippincott, Williams & Wilkins, Philadelphia, PA (1994).

Mack, H. et al., "Design, synthesis and biological activity of novel rigid amidino–phenylalanine derivatives as inhibitors of thrombin," *J. Enzyme Inhibition* 9:73–86 Harwood Academic Publishers, GmbH, Reading, England (1995).

Powers, W.J. et al., "Indium–111 platelet scintigraphy in cerebrovascular disease," *Neurology* 32:938–943 Lippincott, Williams & Wilkins, Philadelphia, Pa (1982).

Saulnier, M.G. et al., "An Effiecient Method for the Synthesis of Guanidino Prodrugs," *Bioorg. Med. Chem. Lett.* 4:1985–990 Pergamon–Elseiver Science Ltd., Oxford, England (1994).

Thakur, M.L. et al., "Indium–111 Labeled Platelets: Studies on Preparation and Evaluation of the In Vitro and In Vivo Functions," *Thrombosis Res.* 9:345–357 Pergamon–Elsevier Science Ltd., Oxford, England (1976).

* cited by examiner

HETEROARYL PROTEASE INHIBITORS AND DIAGNOSTIC IMAGING AGENTS

CROSS-REFERENCE TO RELATED APPLICATION

This application claims the benefit, under 35 U.S.C. §119(e), of the earlier filing date of U.S. Provisional Application No. 60/142,929, filed on Jul. 9, 1999, which is fully incorporated by reference herein.

BACKGROUND OF THE INVENTION

1. Field of the Invention

The present invention relates to novel compounds that function as proteolytic enzyme inhibitors and to their use as diagnostic imaging agents.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Iihibitors as Drugs*, Sandler, ed., University Park Press, Baltimore (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphlylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel ketothiazole aminoguanidine and alkoxyguanidine compounds having Formula I (below). Also provided are processes for preparing compounds of Formula I.

The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating pancreatitis, thrombosis, ischemia, stroke, restenosis or inflammation in a mammal by administering an effective amount of a compound of Formula I.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

The present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

DETAILED DESCRIPTION OF THE PREFERRED EMBODIMENTS

Compounds of the present invention include compounds of Formula I:

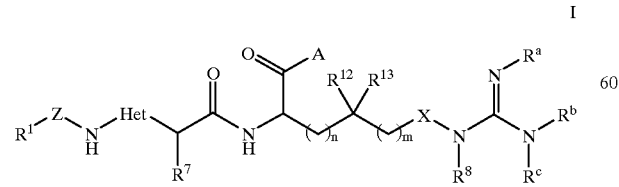

or a solvate, hydrate or pharmaceutically acceptable salt thereof; wherein:

$R^1$ is alkyl, cycloalkyl, cycloalkylalkyl, alkenyl, alkynyl, aryl, aralkyl, heterocycle or heterocycloalkyl, any of which may be optionally substituted;

Z is —$SO_2$—, —OCO—, —CO—, —$NR^2CO$— or a covalent bond, where $R^2$ is hydrogen, alkyl, aralkyl, aryl, hydroxy($C_{2-10}$)alkyl, amino($C_{2-10}$)alkyl, monoalkylamino($C_{2-10}$)alkyl, dialkylamino($C_{2-10}$)alkyl or carboxyalkyl;

Het is selected from the group consisting of

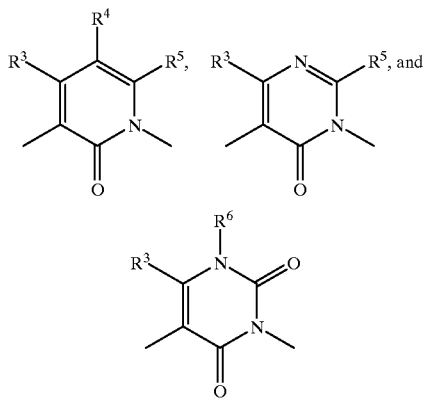

where $R^3$, $R^4$ and $R^5$ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, $CO_2R^x$, —$CH_2OR^x$ or —$OR^x$, where $R^x$, in each instance, is independently one of hydrogen, alkyl or cycloalkyl wherein said alkyl or cycloalkyl groups may optionally have one or more unsaturations;

$R^6$ is hydrogen, alkyl, aralkyl, aryl, cyano($C_{2-10}$)alkyl, hydroxy($C_{2-10}$)alkyl, alkoxy($C_{2-10}$)alkyl, mono- and di-alkylamino($C_{2-10}$)alkyl, or carboxyalkyl;

$R^7$ is hydrogen, $C_{1-4}$alkyl, or $C_{2-4}$ alkenyl;

$R^8$ is hydrogen, alkyl, alkenyl, aralkyl, aryl, hydroxyalkyl, aminoalkyl, monoalkylamino ($C_{2-10}$) alkyl, dialkylamino($C_{2-10}$)alkyl or carboxyalkyl;

$R^{12}$ and $R^{13}$ are independently hydrogen, alkyl, aralkyl, aryl, hydroxyalkyl, aminoalkyl, monoalkylaminoalkyl, dialkylaminoalkyl or carboxyalkyl;

or $R^{12}$ and $R^{13}$ are taken together to form —$(CH_2)_y$—, where y is 2 to 7, preferably 2 to 5;

X is oxygen or $NR^9$, where $R^9$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

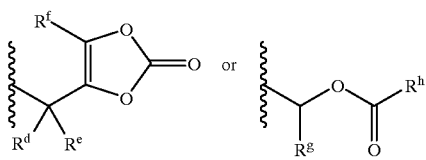

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

A is selected from the group consisting of:

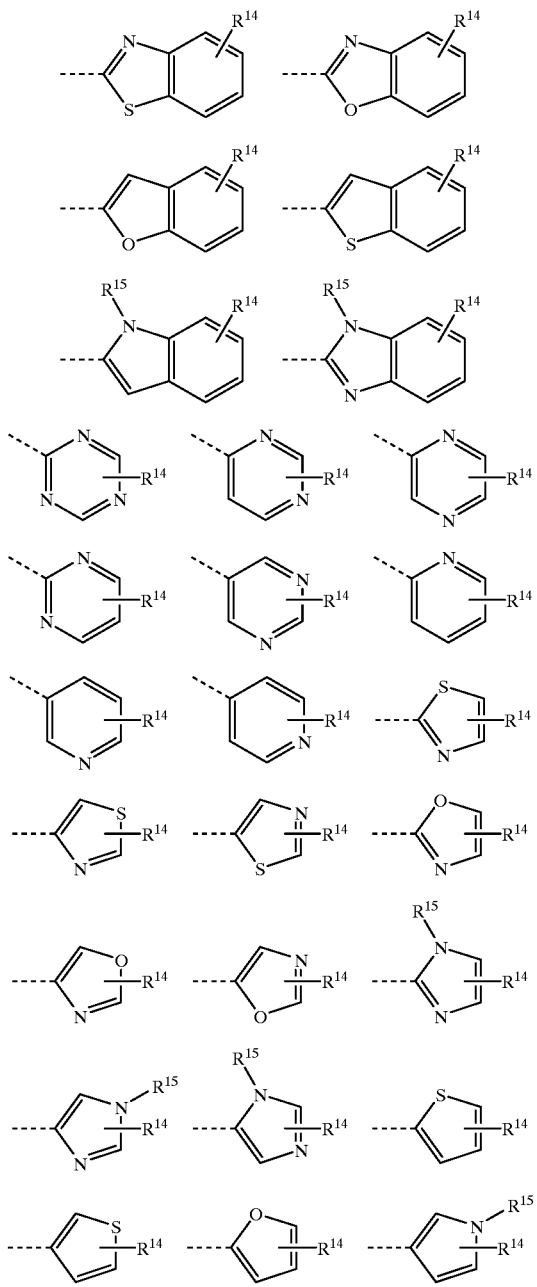

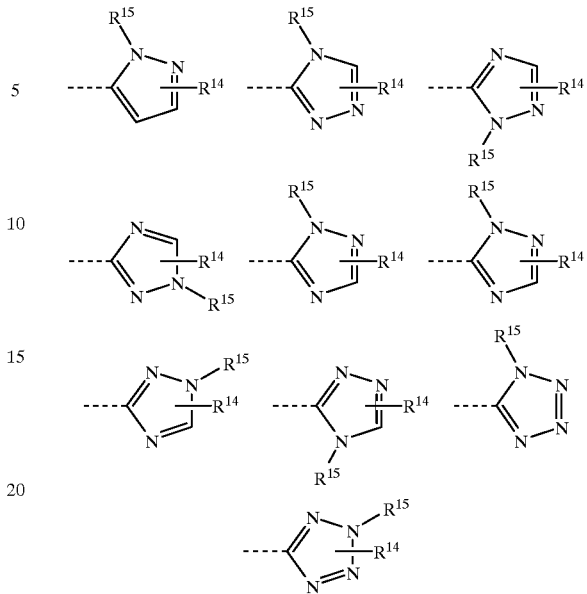

and —N(CH$_3$)—O—CH$_3$, wherein:

$R^{14}$ is hydrogen, $C_{1-6}$ alkyl, carboxy($C_{1-6}$)alkyl, carboxy, $C_{6-20}$ aralkyl, $C_{3-7}$ cycloalkyl, $C_{1-16}$ alkoxycarbonyl, $_{1-16}$ alkoxycarbonyl($C_{1-16}$)alkyl, ($C_{6-10}$)aryl or heteroaryl; $R^{15}$ is hydrogen, $C_{3-7}$cycloalkyl, $C_{1-4}$ alkyl such as methyl, ethyl, propyl or butyl; and the dashed line indicates point of attachment;

n is from zero to 8; and m is from zero to 6.

A preferred group of compounds falling within the scope of the present invention include compounds of Formula I wherein $R^1$ is one of $C_{6-10}$ ar($C_{1-4}$) alkyl, $C_{6-10}$ aryl, $C_{4-7}$ cycloalkyl ($C_{1-4}$)alkyl, heterocycle or heterocyclo($C_{1-4}$) alkyl wherein the heterocycle is a 5- to 7-membered mono- or 9- to 10-membered bicyclic heterocyclic ring that can be saturated or unsaturated, which contains 1 to 3 heteroatoms selected from N, O and S. Any of these $R^1$ groups can be optionally substituted by 1–5, preferably by one, two or three of hydroxy, nitro, trifluoromethyl, halogen, $C_{1-6}$ alkyl, $C_{2-6}$ alkenyl, $C_{6-10}$ aryl, $C_{1-6}$ alkoxy, $C_{6-10}$ ar($C_{1-6}$)alkoxy, amino($C_{1-6}$)alkyl, amino($C_{1-6}$)alkoxy, amino, mono($C_{1-4}$) alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, hydroxy($C_{1-6}$)alkyl, hydroxy($C_{2-6}$)alkoxy, ($C_{1-6}$)alkoxy($C_{2-6}$)alkoxy, mono- and di- $C_{1-4}$ alkylamino($C_{2-6}$)alkoxy, $C_{2-10}$ mono(carboxyalkyl)amino, bis($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{2-4}$,) alkenylsulfonyl, $C_{2-6}$ alkynylsulfonyl, $C_{6-10}$ arylsulfonyl, $C_{6-10}$ ar($C_{1-6}$)alkylsulfonyl, $C_{1-6}$ alkylsulfonyl, $C_{1-4}$ alkylsulfonamido, $C_{6-10}$ arylsulfonamido, $C_{6-10}$ ar($C_{1-6}$)alkylsulfonamido, amidino, guanidino, $C_{1-6}$ alkyliminoamino, formyliminoamino, $C_{2-6}$ carboxyalkoxy, $C_{2-6}$ carboxyalkyl, $C_{2-6}$ carboxyalkylamino, cyano, trifluoromethoxy, or perfluoroethoxy.

An especially preferred group of compounds include compounds of Formula I wherein $R^1$ is phenyl, benzyl, naphthyl, naphthylmethyl, pyridyl, pyridylmethyl, thienyl, thienylmethyl, quinolinyl or quinolinylmethyl, any of which is optionally substituted by one, two or three optional substituents listed in the preceding paragraph, especially halo, such as iodo, chloro or fluoro, methoxy, methyl, trifluoromethyl, cyano, nitro, methylsulfonyl, amino or dimethylamino.

Useful values of $R^1$ include, for example, benzyl, fluorobenzyl, chlorobenzyl, iodobenzyl, dichlorobenzyl, bromobenzyl, trifluoromethylbenzyl, methylsulfonylbenzyl, di(trifluoromethyl)benzyl, methylbenzyl, t-butylbenzyl, methoxybenzyl, dimethoxybenzyl, hydroxybenzyl, carboxybenzyl, aminobenzyl, methylaminobenzyl, n-butylaminobenzyl, amidinobenzyl, guanidinobenzyl, formyliminoaminobenzyl, acetimidoylaminobenzyl, methoxycarbonylbenzyl, ethoxycarbonylbenzyl, carboxymethoxybenzyl, naphthylmethyl, hydroxynaphthylmethyl, cyclohexylmethyl, cyclopentylmethyl, phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, and cyclopentyl. Additional useful values include pyridyl, thienyl, isoquinolinyl, pyridylmethyl, isoquinolinylmethyl, tetrahydroquinolinyl and tetrahydroquinolinylmethyl.

More preferred values of $R^1$ include phenyl, 2-chlorophenyl, 3-chlorophenyl, 4-chlorophenyl, 4-bromophenyl, 3-iodophenyl, 4-iodophenyl, 4-methoxyphenyl, 4-methylphenyl, 2-trifluoromethylphenyl, 4-trifluoromethylphenyl, 2-fluorophenyl, 3-fluorophenyl, 4-fluorophenyl, 3,4-dichlorophenyl, 3-chloro4-fluorophenyl, 3,5-dichlorophenyl, 2-methylphenyl, 3-methylphenyl, 4-ethylphenyl, 2-methylsulfonylphenyl, 4-isopropylphenyl, 3,4-dimethoxyphenyl, 2,4,6-trimethylphenyl, 2,5-dimethylphenyl, 4-vinylphenyl, 2-chloro-6-methylphenyl, 3-bromo-6-methoxyphenyl, 3-chloro-2-methylphenyl, 2-chloro-5-trifluoromethylphenyl, 2,4-dichlorophenyl, 2-butoxy-5-(1,1-dimethylpropyl)phenyl, 3-nitrophenyl, 4-chloro-3-nitrophenyl, 4-methylcarbonylaminophenyl, 4-tert-butylphenyl, 3-cyanophenyl, 4-methylsulfonylphenyl, pentafluorophenyl, 2,5-dichlorophenyl, 2,4-dimethoxyphenyl, 2-methyl-5-nitrophenyl, 3-chloro-2-cyanophenoxy)phenyl, 2-chloro-4-fluorophenyl, 3-chloro-6-methoxyphenyl, 2-methoxy-5-methylphenyl, 4-phenylphenyl, 2-propylbutyl, 5-chloro-2-methoxyphenyl, 2-cyanophenyl, 2-(N-hydroxy)aminophenyl, 2-(4-biphenylmethoxy)phenyl, 2-(3-biphenylmethoxy)phenyl, benzyl, 2-(phenylsulfonyl)phenyl, 2,4-bis(methylsulfonyl)phenyl, 2-chloro-4-methylsulfonylphenyl, benzyl, 3-chlorobenzyl, 3-trifluoromethylbenzyl, 2-trifluoromethylbenzyl, 2-iodobenzyl, 2-chlorobenzyl, 2-bromobenzyl, 3-iodobenzyl, 3-fluorobenzyl, 4-chlorobenzyl, 2-chloro-6-fluorobenzyl, 2-fluorobenzyl, 2,3-dichlorobenzyl, 3,4-difluorobenzyl, 2,4-dichlorobenzyl, 2,5-dichlorobenzyl, 3,4-dichlorobenzyl, 2-methylbenzyl, 5-chloro-2-methoxybenzyl, 2-cyanobenzyl, 2-(4-biphenylmethoxy)benzyl, 2-(3-biphenylmethoxy)benzyl, 2-(phenylsulfonyl)benzyl, 2,4-bis(methylsulfonyl)benzyl, 3-methylsulfonylbenzyl, 2-chloro-4-methylsulfonylbenzyl, 1-naphthalenylmethyl, 2-naphthalenylmethyl, and 2-naphthalenyl.

Additional preferred values of $R^1$ include dansyl, thien-2-yl, pyridin-2-yl, 3-methylquinolin-1-yl, 1-methylimidazol-4-yl, quinolin-5-yl, quinoline-8-yl, 6-bromonaphthalen-2-yl, 6-chloronaphthalen-2-yl, 5-chlorothien-2-yl, 5-methyl-8-quinolinyl, 8-quinolinylmethyl, 5-methyl-8-quinolinylmethyl, 4-benzo-2,1,3-thiadiazolyl, and 5-chloro-1,3-dimethyl-4-pyrazolyl.

Preferred values of $R^2$ in Formula I include hydrogen, $C_{1-6}$ alkyl, $C_{6-10}$ ar($C_{1-6}$)alkyl, $C_{6-10}$ aryl, hydroxy($C_{2-10}$) alkyl, amino($C_{2-10}$)alkyl, $C_{2-7}$ carboxyalkyl, mono($C_{1-4}$ alkyl)amino($C_{2-8}$)alkyl, and di($C_{1-4}$ alkyl)amino($C_{2-8}$)alkyl. Suitable values of $R^2$ include hydrogen, methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino)ethyl, with hydrogen being most preferred.

Preferred Het groups include

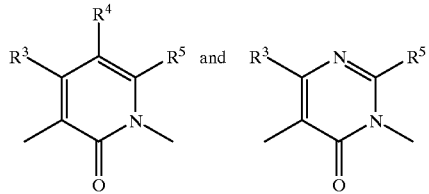

Preferred compounds are those where $R^3$, $R^4$ and $R^5$ are independently hydrogen, $C_{1-4}$ alkyl, $C_{3-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl, or cycloalkyloxycarbonyl.

Useful values of $R^3$, $R^4$ and $R^5$ include hydrogen, methyl, ethyl, propyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl.

Preferred $R^3$ and $R^4$ groups include hydrogen, $C_{1-12}$ alkyl, and $C_{2-6}$ alkenyl. A most preferred value of $R^3$ and $R^4$ is hydrogen.

Preferred $R^5$ groups include hydrogen, halogen, $C_{1-5}$ alkyl, $C_{3-6}$ alkenyl, $C_{3-5}$ cycloalkyl, trifluoromethyl, and $C_{1-4}$ alkoxy, more preferably $C_{1-4}$ alkyl, such as methyl, ethyl, propyl or isopropyl.

A particularly preferred Het, when $R^3$ and $R^4$ are independently selected to be hydrogen or methyl, is

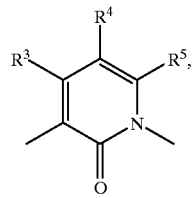

wherein $R^5$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrolyl, 3-pyrolyl, 1-hexyl, S-2-hexyl, R-2-hexyl, R-3-hexyl, and S-3-hexyl. A particularly preferred Het according to this aspect has hydrogen, methyl, ethyl, propyl or isopropyl as $R^5$.

Preferred values of Z include —$SO_2$— and a covalent bond.

A preferred $R^7$ group is hydrogen.

Preferred values of $R^{14}$ are hydrogen, $C_{1-4}$alkyl, carboxy and carboxy($C_{1-4}$)alkyl. $R^{15}$ is preferably hydrogen or $C_{1-4}$alkyl.

A preferred value of A is:

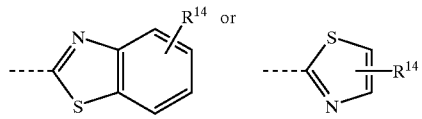

wherein $R^{14}$ is H or $C_{1-4}$ alkyl such as methyl, ethyl, propyl or butyl and most preferably wherein $R^{14}$ is hydrogen.

Preferred compounds are those of Formula I, where $R^8$ is hydrogen, $C_{1-4}$ alkyl or $C_{6-10}$ aryl($C_{1-6}$)alkyl.

Preferred compounds when X is $NR^9$ are those wherein $R^9$ is hydrogen or $C_{1-6}$ alkyl, optionally substituted by one, two or three, preferably one, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^9$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Most preferred compounds are those where X is oxygen.

Preferred compounds are those of Formula I, where $R^{12}$ and $R^{13}$ are independently one of hydrogen, $C_{1-6}$ alkyl, $C_{6-10}$ ar($C_{1-6}$)alkyl, $C_{6-10}$ aryl, hydroxy($C_{2-10}$)alkyl or $C_{2-7}$ carboxyalkyl. Useful values of $R^{12}$ and $R^{13}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those where $R^{12}$ and $R^{13}$ are taken together to form —$(CH_2)_y$— where y is 2–5.

Preferred values of $R^a$, $R^b$ and $R^c$ in Formula I are independently hydrogen, hydroxy, $C_{1-6}$alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

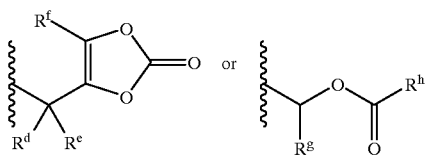

where $R^d$–$R^h$ are defined as above. When $R^a$, $R^b$ and $R^c$ are —$CO_2R^w$, where $R^w$ is one of one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula I include from zero to 6, more preferably from zero to 4, and most preferably zero, 1 or 2.

Preferred values of m are from zero to 4, most preferably zero, 1 or 2.

In the most preferred compounds m is zero or 1, and n is zero or 1.

According to a particularly preferred aspect, provided are compounds of Formula I wherein Z is —$SO_2$—, $R^1$ is substituted or unsubstituted aryl or aralkyl; Het is

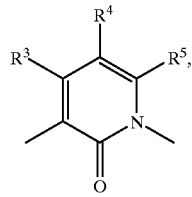

where $R^3$ and $R^4$ are each hydrogen and $R^5$ is methyl; X is O; $R^8$ is hydrogen, $C_{1-6}$ alkyl or $C_{6-10}$ aryl ($C_{1-6}$)alkyl; and $R^a$, $R^b$ and $R^c$ are all hydrogen. A very preferred aspect is directed to such compounds where $R^1$ is substituted or unsubstituted benzyl or phenyl; $R^3$ and $R^4$ are each hydrogen and $R^5$ is methyl; X is O; $R^8$ is hydrogen, $C_{1-6}$ alkyl, or $C_{6-10}$ aryl ($C_{1-6}$)alkyl; and $R^a$, $R^b$ and $R^c$ are all hydrogen.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$ and/or $R^c$ are —$CO_2R^w$, where $R^w$ is defined above. See U.S. Pat. No. 5,466,811 and Saulnier et al., Bioorg. Med. Chem. Lett. 4:1985–1990 (1994).

When any variable occurs more than one time in any constituent or in Formula I, its definition on each occurrence is independent of its definition at every other occurrence. Also, combinations of substituents and/or variables are permissible only if such combinations result in stable compounds.

The present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention includes methods which are useful for in vivo imaging of thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a meta I-123, meta I-125 or meta I-131 substitution, or benzyl, having an ortho I-123, ortho I125 or ortho I131 substitution.

The detectable label can also be a radioactive or paramagnetic chelate in which a suitable ligand (L) is attached to an $R^1$ substituent, either directly or via a divalent linking group A". Alternatively, the group —A"—L substitutes for the groups —Z—$R^1$ in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, —C(=NH)—(CH$_2$)$_6$—C(=NH)—, —C(=O)—(CH$_2$)$_6$—C(=O)—,

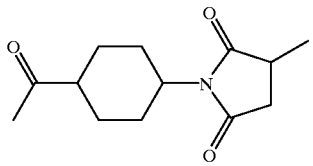

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., *Science* 209:295 (1980); Paik C. H. et al., U.S. Pat. No. 4,652,440 (1987); Gries, H. et al., U.S. Pat. No. 4,957,939 (1990). A preferred chelating ligand, L, is 1-(p-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic orbicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to C$_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "C$_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The terms "alkoxy" refers to any of the above alkyl groups linked to an oxygen atom.

The term "halogen" or "halo" as employed herein by itself or as part of another group refers to chlorine, bromine, fluorine or iodine, with iodine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes 1 and 2 outline the synthesis of compounds of the present invention where $R^1$—Z is $R^1$—$SO_2$—.

Scheme 1

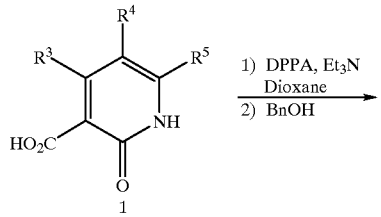

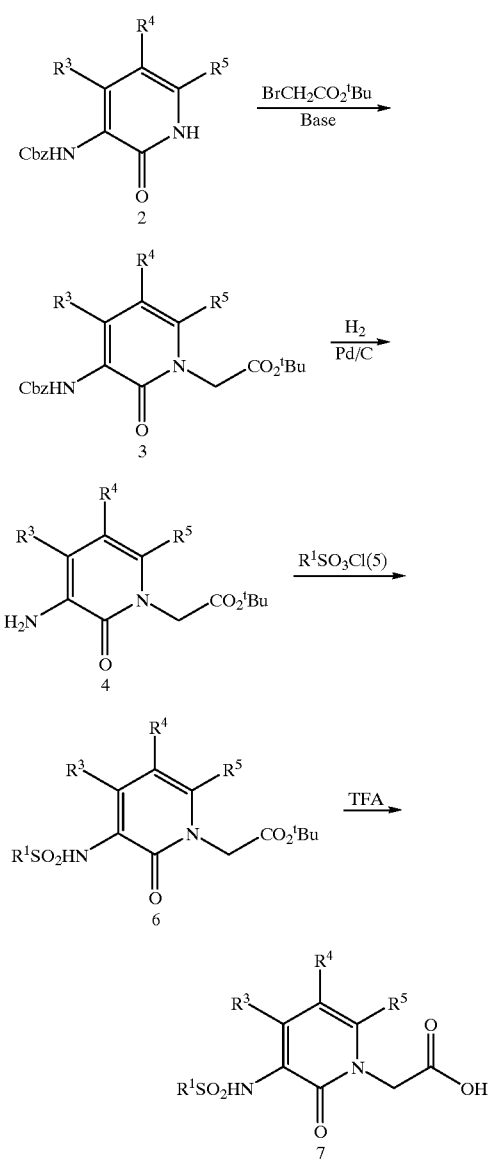

Scheme 2

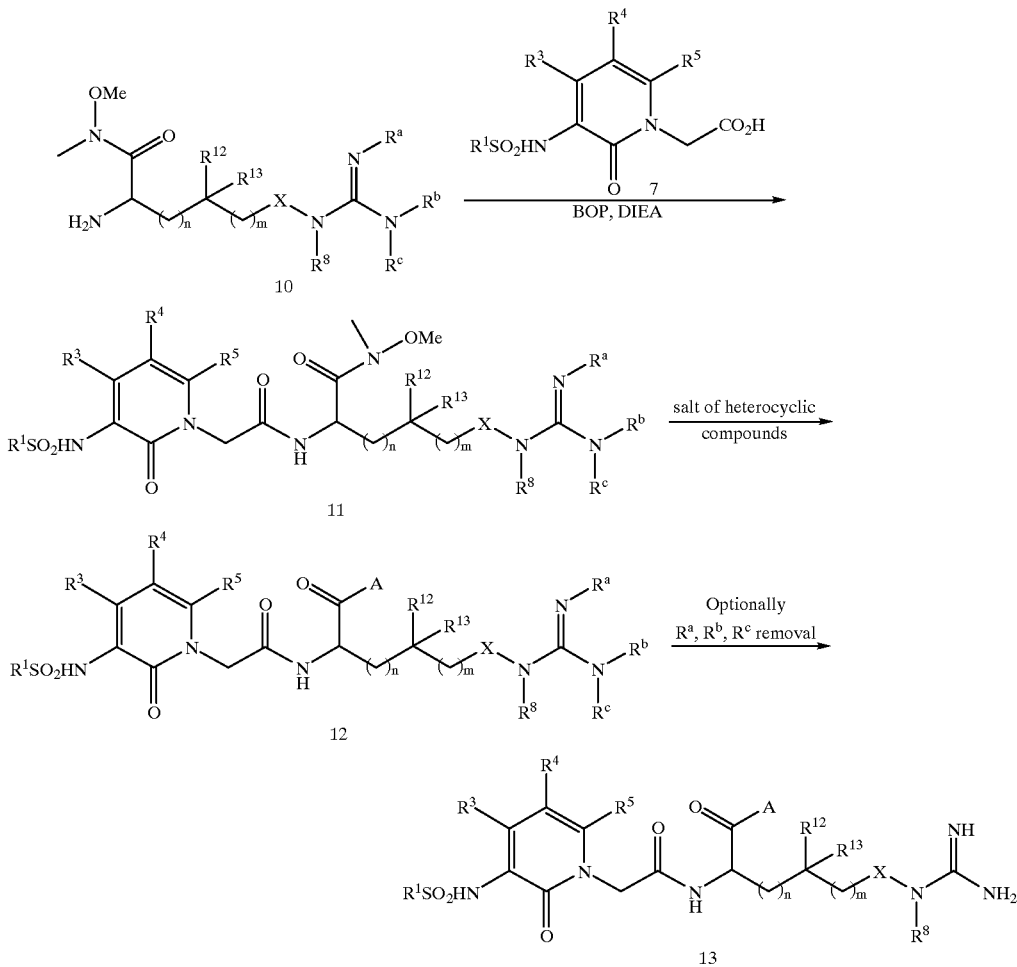

In Scheme 1, the 2-hydroxypyridine carboxylic acid 1 is reacted with diphenylphosphoryl azide (DPPA), triethylamine, and benzyl alcohol in a suitable solvent, such as dioxane, to give protected amino pyridonone 2. Compound 2 is then alkylated with a glycine equivalent, such as tert-butyl bromoacetate, in the presence of a base, such as cesium carbonate, or lithium hexamethyldisilazide, in an appropriate solvent, such as tetrahydrofuran (THF) or N,N-dimethylformamide (DMF), to generate alkylated pyridinone 3. The Cbz protecting group is removed under standard hydrogenation conditions, such as palladium on activated carbon in ethanol or methanol under hydrogen, to produce 3-amino pyridinone 4. The free amino group in structure 4 is then sulfonated using alkyl—, aralkyl—, or arylsulfonyl chloride 5 in the presence of an appropriate base, such as N-methyl morpholine, triethylamine, ordiisopropylethylamine (DEA) in a suitable solvent, such as dichloromethane (DCM) or acetonitrile, to give sulfonamide 6. The tert-butyl group in 6 is then removed under standard conditions well known in the art (Greene, T. W., and Wuts, P. G. W., *Protecting Groups in Organic Synthesis*, 2nd edition, John Wiley and Sons, Inc. New York, 1991), such as trifluoroacetic acid in DCM or hydrochloric acid gas in ethyl acetate, to release free acid 7.

To form a radioiodinated compound of the invention, radioiodinated aryl or aralkyl sulfonyl chlorides can be employed as reagent 5.

In Scheme 2, the protected compound 8 (Pajpanova, T., et. al., *Amino Acids* 12:191–204 (1997)) is activated by coupling with N,O-dimethylhydroxylamine hydrochloride in the presence of BOP in DMF, to afford Weinreb type of amide 9 (Nahm, S., and Weinreb, M., *Tetrahedron Lett.* 22:3815 (1981)). The Cbz group of 9 is removed under mild catalytic hydrogenation conditions, such as Pd/C in the presence of several equivalents of chloroform in methanol under hydrogen to generate 10. Amine 10 is coupled with acid 7 in the presence of a typical peptide coupling reagent, such as Castro's reagent (BOP), and a base, such as DIEA, in a suitable solvent, such as DMF to produce amide 11. Coupling of N,N-methoxymethyl amide 11 with lithiated heterocyclic compounds, such as thiazole or benzothiazole, in an appropriate solvent, such as THF, generates α-heterocyclic keto compound 12. Finally, the O-guanidine group of compound 12 is unmasked by treating compound 12 with typical reagents for Boc deprotection, such as TFA, in a suitable solvent, such as DCM, to afford compound 13.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent forquantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula I can be labeled with radioactive iodine as described below in Example 3 or by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. In particular, technetium-99m (Tc-99m) is an ideal radioactive atom for imaging because of its nuclear properties. It is a gamma emitter and has a single photon energy of 140 keV, a half-life of about 6 hours, and it is readily available from a Mo-99/Tc-99 generator. Rhenium-186 and -188 also have gamma emission which allows them to be imaged. Preferred compositions contain the radioactive atom, Tc-99m.

Compositions of the present invention are conveniently prepared by completing a compound of Formula I with radioisotopes which are suitable for detection externally.

The compounds of Formula I can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 $\mu$g to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

The source of technetium-99m should preferably be water soluble. Preferred sources are alkali and alkaline earth metal pertechnetate ($TcO_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. For example, stannous chloride ($SnC_{1-2}$) is the reducing agent and can be used in range from 1–1,000 $\mu$g/mL. Especially preferred concentrations are about 30–500 $\mu$g/mL.

Citric acid complexes with technetium-99m to quickly form a stable technetium-99m-citrate complex. Upon contact with a compound of Formula I, substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 $\mu$g/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

Alternative compositions of the present invention include an In-111 labeled compound of the present invention.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysprosium (III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of a radiolabeled compound of Formula I. Compositions such as those described above may be conveniently used in these diagnostic compositions.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 $\mu$Ci, preferably about 10 $\mu$Ci. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, Remington's Pharmaceutical Sciences, Mack Publishing Co. (A. R. Gennaro edit. 1985).

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are

EXAMPLE 1

N-{((S)-1-[2-(Amidinoaminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide

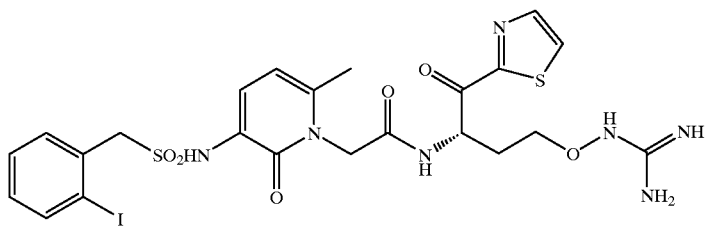

1. 3-Benzyloxycarbonylamino-6-methyl-2-pyridinone

Diphenylphosphoryl azide (11.9 mL, 55 mmol) was added to a solution of 2-hydroxy-6-methylpyridine-3-carboxylic acid (7.65 g, 50 mmol) and triethylamine (7.7 mL, 55 mmol) in dry dioxane (100 mL) and the resulting solution was heated to reflux. After 16 h additional triethylamine (7.7 mL, 55 mmol) and benzyl alcohol (5.7 mL, 50 mmol) were added and the solution was refluxed for a further 24 h. The reaction mixture was concentrated in vacuo and the residue was partitioned between methylene chloride (200 mL) and brine (100 mL), and acidified to pH 1 with 10% HCl. The organic layer was washed with saturated NaHCO$_3$ (2×100 mL), brine (100 mL), dried over Na$_2$SO$_4$, and filtered.

After evaporating the solvent in vacuo, methanol (100 mL) and hexane (20 mL) were added to the residue, the solid was collected, washed with methanol (50 mL) and dried to give the title compound as a white solid (7.2 g, 56%). $^1$H NMR (300 MHz, CDCl$_3$) δ 12.82 (s, 1H), 8.06 (d, J=7.0 Hz, 1H), 7.69 (s, 1H), 7.42 (m, 5H), 6.09 (d, J=7.5 Hz, 1H), 5.22 (s, 2H), 2.32 (s, 3H).

2. 3-Benzyloxycarbonylamino-6-methyl-1-(tert-butoxycarbonylmethyl]-2-pyridinone

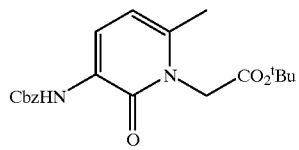

tert-Butyl bromoacetate (3.9 g, 20 mmol) was added to a stirred suspension of 3-benzyloxycarbonylamino-6-methyl-2-pyridinone (5.15 g, 20 mmol), as prepared in the preceding step, and Cs$_2$CO$_3$ (6.5 g, 20 mmol) in N,N-dimethylformamide (50 mL) and stirred at 40° C. overnight. The solid was removed by filtration and the filtrate concentrated under high vacuum. The residue was dissolved in ethyl acetate (150 mL), washed with water (2×50 mL), brine (50 mL), dried over Na$_2$SO$_4$, and concentrated in vacuo. After evaporating the solvent in vacuo, the residue was purified by flash column chromatography (25% ethyl acetate in hexane) to give the title compound as a white crystalline solid (4.2 g, 56%). $^1$H-NMR (300 MHz, CDCl$_3$) δ 7.95 (d, J=7.3 Hz, 1H), 7.76 (s, 1H), 7.37 (m, 5H), 6.09 (d, J=7.6 Hz, 1H), 5.19 (s, 2H), 4.75 (s, 2H), 2.32 (s, 3H), 1.47 (s, 9H).

3. 3-Amino-6-methyl-1-(tert-butyloxycarbonylmethyl)-2-pyridinone

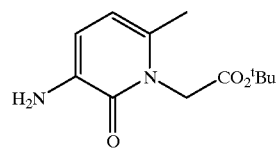

A mixture of 3-benzyloxycarbonylamino-6-methyl-1-(tert-butoxycarbonylmethyl)-2-pyridinone (4.1 g, 11 mmol), as prepared in the preceding step, and 10% Pd/C (400 mg) in ethanol (100 mL) was hydrogenated under hydrogen (balloon) for 1.5 h. The catalyst was removed by filtration through Celite and the filtrate concentrated to give the title compound as a white solid (2.55 g, 97%). $^1$H-NMR (300 MHz, CDCl$_3$) δ 6.49 (d, J=7.3 Hz, 1H), 5.92 (d, J=7.3 Hz, 1H), 4.75 (s, 2H), 2.19 (s, 3H), 1.47 (s, 9H).

4. tert-Butyl 2-[3-({[(2-Iodophenyl)methyl]sulfonyl}amino)-6-methyl-2-oxohydropyridyl]acetate

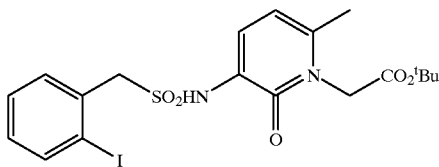

To a solution of 3-amino-6-methyl-1-(tert-butyloxycarbonylmethyl)-2-pyridinone (5.04 g, 1.48 mmol), as prepared in the preceding step, and 4-methylmorpholine (326 μL, 2.97 mmol) in DCM (7 mL) was added 2-iodobenzyl sulfonyl chloride (0.496 g, 1.48 mmol) and stirred at 0° C. for 1 h. The reaction mixture was then diluted with DCM (7 mL), washed with saturated NaHCO$_3$ (2×20 mL), 10% citric acid (3×20 mL), brine (20 mL), dried over Na$_2$SO$_4$, and concentrated to give crude product as a yellow solid. The solid was washed with EtOAc/hexane (1:2,2×10 mL) to deliver the title compound (0.63 g, 82% yield) as a white solid. $^1$H NMR (300 MHz, CDCl$_3$) δ 7.82 (dd, J=1.16 and 7.97 Hz, 1H), 7.43–7.27 (m, 4H), 6.98 (dt, J=1.66 and 7.60 Hz, 1H), 6.01 (dd, J=0.63 and 7.67 Hz, 1H), 4.74 (s, 2H), 4.56 (s, 2H), 2.25 (d, J=0.51 Hz, 3H), 1.47 (s, 9H).

5. 2-[3-({([(2-Iodophenyl)methyl]sulfonyl}amino)-6-methyl-2-oxohydropyridyl]acetic Acid

To tert-butyl-2-[3-({[(2-iodophenyl)methyl]sulfonyl}amino)-6-methyl-2-oxohydropyridyl]acetate (200 mg, 0.39 mmol), as prepared in the preceding step, was added a solution of TFA in DCM (4 mL, 1/3 (v/v)). After stirring at room temperature for 4 h, solvent was removed. The resulting solid was then washed with Et$_2$O to deliver the title compound (172 mg, 96% yield) as a white solid. Mass spectrum (LCMS, ESI) calcd. for C$_{15}$H$_{16}$IN$_2$O$_5$S 463.0 (M+H); found: 463.1. $^1$H-NMR (300 MHz, DMSO-d$_6$) δ 8.99 (s, 1H), 7.89 (dd, J=1.03 and 7.88 Hz, 1H), 7.53 (dd, J=1.62 and 7.71 Hz, 1H), 7.38 (dt, J=1.1 and 7.49 Hz, 1H), 7.23 (d, J=7.50 Hz, 1H), 7.08 (dt, J=1.69 and 7.73 Hz, 1H), 6.15 (d, J=7.70 Hz, 1H), 4.79 (s, 2H), 4.65 (s, 2H), 2.28 (s, 3H).

6. (2S)-4-({[(tert-Butoxy)carbonylamino]iminomethyl}aminooxy)-2-[(phenylmethoxy)carbonylamino]butanoic Acid

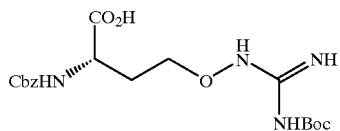

(2S)-4-(Amidinoaminooxy)-2-[(phenylmethoxy)carbonylamino]butanoic acid (Pajpanova, T., et. al., Amino Acids 12:191–204 (1997)) (0.45 g, 1.5 mmol) was dissolved in a solution of Na$_2$CO$_3$ (0.92 g) in 8.7 mL of H$_2$O, then a solution of Boc$_2$O (0.35 g, 1.6 mmol) in dioxane (8.7 mL) was added with stirring. After 4 hours, additional Boc$_2$O (0.35 g) was added, and the reaction mixture was stirred overnight. At this point, all starting (2S)-4-(amidinoaminooxy)-2-[(phenylmethoxy)carbonylamino] butanoic acid was consumed, as indicated in TLC using DCM:MeOH:H$_2$O (80:30:5). Organic solvent was removed under reduced pressure. The resulting mixture was cooled in an ice-water bath, acidified to pH 2–3 with KHSO$_4$, and extracted with EtOAc (4×100 mL). The organic extracts were combined, washed with brine, dried over Na$_2$SO$_4$, and concentrated. The product was precipitated by addition of hexane, and further purified by recrystallization from EtOAc/hexane, providing the title compound (0.49 g, 82% yield) as a white solid. Mass spectum (LCMS, ESI) calcd. for C$_{18}$H$_{27}$N$_4$O$_7$ (M+H) 411.4; found: 410.9. $^1$H-NMR (300 MHz, DMSO-d$_6$) δ 12.55 (bs, 1H), 9.26 (bs, 1H), 7.60 (d, J=7.99 Hz, 1H), 7.37–7.23 (m, 6H), 6.04 (bs, 2H), 5.03 (s, 2H), 4.10–4.03 (m, 1H), 3.76 (bt, J=5.67 Hz, 2H), 2.13–2.07 (m, 1H), 1.82–1.72 (m, 1H), 1.41 (s, 9H).

7. (2S)-4-({[(tert-Butoxy)carboizylamnino]iminomethyl}aminooxy)-N-methoxy-N-methyl-2-[(phenylmethoxy)carbonylamino]butanamide

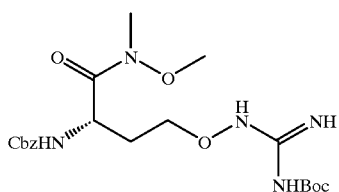

To a solution of (2S)-4-({[(tert-butoxy)carbonylamino]iminomethyl}aminooxy)-2-[(phenylmethoxy)carbonylamino]butanoic acid (300 mg, 0.73 mmol), as prepared in the preceding step, in DMF (3.0 mL) at 0° C. was added the HCl salt of MeNH(OMe) (146 mg, 1.5 mmol), DIEA (0.90 mL, 5.2 mmol), and BOP (340 mg, 0.77 mmol), and stirred for 10 h at 0° C. The reaction mixture was allowed to warm up to rt and stirred for 6 h. After removal of solvents in high vacuo, the resulting residue was partitioned between EtOAc (300 mL) and H$_2$O (30 mL). The organic layer was washed with saturated NaHCO$_3$ (20 mL), H$_2$O (20 mL), 10% KHSO$_4$ (20 mL), brine (2×20 mL), dried over Na$_2$SO$_4$, concentrated, and filtered through a short path silica gel column, eluting with MeOH in DCM (0, 2.5 to 5%). The filtrate was concentrated to afford the title compound (329 mg, 99% yield) as a white solid. Mass spectrum (LCMS, ESI) calcd. for C$_{20}$H$_{32}$N$_5$O$_7$ 454.2 (M+H); found: 454.0.

8. (2S)-2-Amino-4-({[(tert-butoxy)carbonylamino]iminomethyl}aminooxy)-N-methoxy-N-methylbutanamide

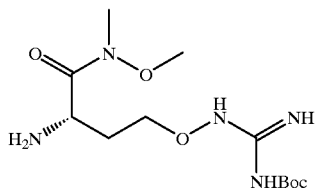

A suspension of (2S)-4-({[(tert-butoxy)carbonylamino]iminomethyl}aminooxy)-N-methoxy-N-methyl-2-[(phenylmethoxy)carbonylamino] butanamide (120 mg, 0.27 mmol), as prepared in the preceding step, and 10% Pd/C (18 mg) in methanol (5.0 mL) and chloroform (158 mL, 1.32 mmol) was hydrogenated with a balloon until all starting amine was consumed (in about 6 to 7 h). The mixture was filtered through Celite. The filtrate was concentrated to give the title compound (80 mg, 95% yield) as a colorless oil. Mass spectrum (LCMS, ESI) calcd. for $C_{12}H_{26}N_5O_5$ 320.4 (M+H); found: 320.0.

9. (2S)-4-({[(tert-Butoxy)carbonylamino]iminomethyl}aminooxy)-2-{2-[3-({[(2-iodophenyl)methyl]sulfonyl}amino}-6-methyl-2-oxohydropyridyl]acetylamino)-N-methoxy-N-methylbutanamide

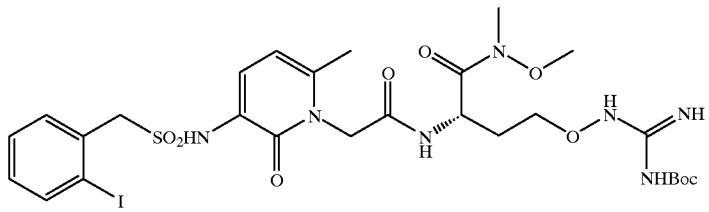

To a DMF solution of the amine (2S)-2-amino-4-({[(tenbutoxy)carbonylamino]iminomethyl}aminooxy)-N-methoxy-N-methylbutanamide (28 mg, 88 μmol), as prepared in the preceding step, was added 2-[3-({[(2-iodophenyl)methyl]sulfonyl}amino)-6-methyl-2-oxohydropyridyl]acetic acid (43 mg, 92.7 μmol), as prepared in step 5, DIEA (80 mg, 618 μmol), and BOP (943 mg, 97.1 μmol) at 0° C. After stirring at 0° C. for 10 h, the reaction mixture was allowed to warm up to rt and stirred for an additional 16 h. Solvents were removed. The mixture was partitioned between EtOAc (80 mL) and $H_2O$ (20 mL). The aqueous layer was back extracted with EtOAc (40 mL). Organic layers were combined, washed with saturated $NaHCO_3$ (2×20 mL), brine (2×20 mL), dried over $Na_2SO_4$, concentrated, and flash chromatographed in silica gel, eluting with MeOH/DCM (0, 2.5, and 5%) to give the title compound (49 mg, 73% yield) as an oil. Mass spectrum (LCMS, ESI) calcd. for $C_{27}H_{39}IN_7O_9S$ 764.2 (M+H); found: 763.8. $^1H$ NMR (300 MHz, $CD_3OD$) δ 7.84 (d, J=7.87 Hz, 1H), 7.49 (dd, J=1.37 and 7.68 Hz, 1H), 7.40 (d, J=7.63 Hz, 1H), 7.33 (t, J=7.55 Hz, 1H), 7.00 (dt, J=1.56 and 7.77 Hz, 1H), 6.17 (d, J=7.69 Hz, 1H), 5.09 (bd, J=5.80 Hz, 1H), 4.98 (d, J=16.27 Hz, 1H), 4.85 (d, J=16.27 Hz, 1H), 4.65 (s, 2H), 3.91 (bd, J=6.79 Hz, 2H), 3.75 (s, 3H), 3.18 (bs, 3H), 2.33 (s, 3H), 2.24–2.12 (m, 1H), 1.89–1.78 (m, 1H), 1.46 (s, 9H).

10. N-{(1S)-1-[2-({[(tert-Butoxy)carbonylamino]iminomethyl}aminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide

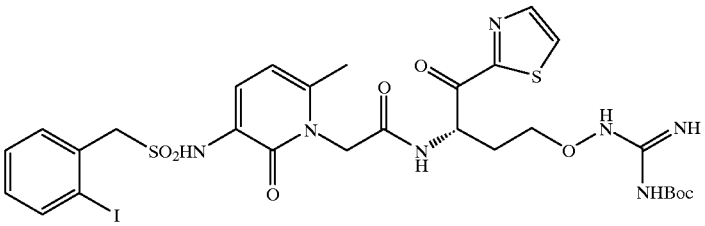

To a solution of thiazole (60.4 mg, 710 μmol) in THF (0.9 mL) at −78° C. was added n-butyl lithium and stirred for 30 minutes. To this dark yellow mixture was added a solution of (2S)-4-({[(tert-butoxy)carbonylamino]iminomethyl}aminooxy)-2-{2-[3-({[(2-iodophenyl)methyl]sulfonyl}amino)-6-methyl-2-oxohydropyridyl]

acetylamino}-N-methoxy-N-methylbutanamide (45 mg, 59 μmol), as prepared in step 9, in THF (0.6 mL) over a period of 3 minutes. After stirring at the same temperature for 2.5 h, 1N HCl (0.5 mL) was added to quench the reaction. The mixture was allowed to warm up to rt and diluted with EtOAc (50 mL), washed with 1N HCl (5 mL) and brine (5 mL), dried over $Na_2SO_4$, concentrated, and flash chromatographed in silica gel eluting with 0–3.5% methanol in dichloromethane (MeOH/DCM) to afford the title compound (21 mg, 45% yield) as an oil. Mass spectrum (LCMS, ESI) calcd. for $C_{28}H_{35}IN_7O_8S_2$ 788.1 (M+H); found: 787.8.

11. N-{(1S)-1-[2-(Amidinoaminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide To N-{(1S)-1-[2-({[(tert-butoxy)carbonylamino]iminomethyl}aminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide (18 mg, 22.8 μmol), as prepared in the preceding step, was added a solution of TFA in DCM (1.5 mL, 1/1 (v/v)) and stirred at rt for 3 h. Solvents were evaporated, and the crude product (orange oil) was purified by flash chromatography on silica gel, eluting with 10% MeOH/DCM to provide the title compound (8 mg, 44% yield). Mass spectrum (LCMS, ESI) calcd. for $C_{23}H_{37}IN_7O_6S_2$ 688.0 (M+H); found: 688.0. $^1$H NMR (300 MHz, $CD_3OD$) δ 8.11 (d, J=1.46 Hz, 1H), 8.06 (d, J=3.05 Hz, 1H), 7.86 (dd, J=1.19 and 7.96 Hz, 1H), 7.50 (dd, J=1.63 and 7.74 Hz, 1H), 7.38 (d, J=7.64 Hz, 1H), 7.35 (dt, 1.23 and 7.53 Hz, 1H), 7.03 (dt, 1.72 and 7.71 Hz, 1H), 6.19 (dd, 0.65 and 7.64 Hz, 1H), 5.82 (dd, 3.79 and 10.16 Hz, 1H), 5.49 (s, 2H), 5.02 (d, J=16.35 Hz, 1H), 4.83 (d, J=16.35 Hz, 1H), 4.67 (s, 2H), 4.16–4.03 (2H), 2.62–2.51 (m, 1H), 2.33 (s, 3H), 2.08–1.96 (m, 1H).

EXAMPLE 2

N-{(1S)-1-[2-(Amidinoaminooxy)ethyl]-2-betzothiazol-2-yl-2-oxoethyl}-2-[3-({[(2-iodophenyl)methyl]sulfonyl}amino)-6-methyl-2-oxohydropyridyl]acetamide 1. N-{(1S)-2-Benzothiazol-2-yl-1-[2-({[(tert-Butoxy)carbonylamino]iminomethyl}aminooxy)ethyl]-2-oxoethyl}-2-[3-({[(2-iodophenyl)methyl]sulfonyl}amino)-6-methyl-2-oxohydropyridyl]acetamide

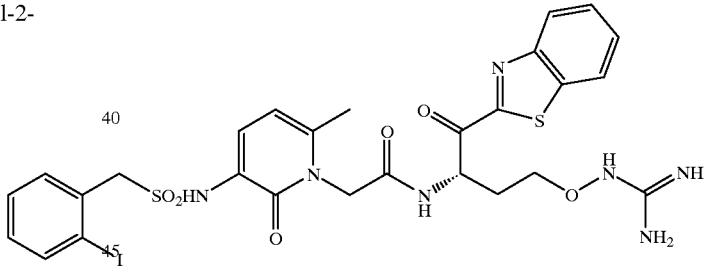

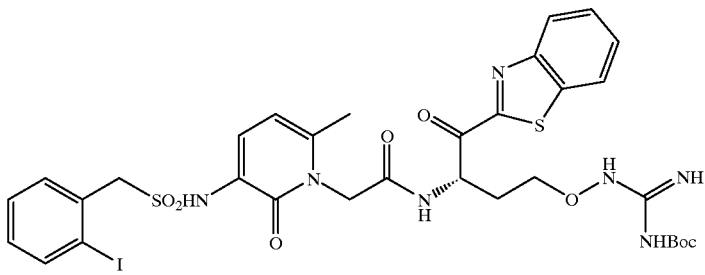

The title compound was prepared via coupling of (2S)-4-({[(tert-butoxy)carbonylamino]iminomethyl}aminooxy)-2-{2-[3-({[(2-iodophenyl) methyl]sulfonyl}amino)-6-methyl-2-oxohydropyridyl]acetylamino}-N-methoxy-N-methylbutanamide, as prepared in step 9 of Example 1, with lithiated benzothiazole using the same experimental procedure as in step 10 of Example 1. Mass spectrum (LCMS, ESI) calcd. for $C_{32}H_{37}N_7O_8S_2$ 838.1 (M+H); found: 837.9. $^1$H NMR (300 MHz, $CD_3OD$) δ 8.21–8.15 (m, 1H), 8.09–8.04 (m, 1H), 7.82 (dd, J=1.19 and 7.97 Hz, 1H), 7.62–7.54 (2H), 7.46 (dd, J=1.64 and 7.74 Hz, 1H), 7.39 (d, J=7.61 Hz, 1H), 7.31 (dt, J=1.23 and 7.53 Hz, 1H), 6.97 (dt, J=1.68 and 7.70 Hz, 1H), 6.15 (dd, J=0.61 and 7.65 Hz, 1H), 5.87 (dd, J=4.34 and 9.85 Hz, 1H), 5.03 (d, J=16.28 Hz, 1H), 4.90 (d, J=15.84 Hz, 1H), 4.63 (s, 2H), 4.01 (t, J=5.24 Hz, 2H), 2.56–2.45 (m, 1H), 2.31 (s, 3H), 2.20–2.09 (m, 1H), 1.46 (s, 9H).

2. N-{(1S)-1-[2-(Amidinoaminooxy)ethyl]-2-benzothiazol-2-yl-2-oxoethyl}-2-[3-({[(2-iodophenyl)methyl]sulfonyl}amino)-6-methyl-2-oxohydropyridyl]acetamide oxohydropyridyl]acetamide, as prepared in the preceding step, by removing Boc group using the same experimental procedure as in step 11 of Example 1. Mass spectrum (LCMS, ESI) calcd. for $C_{27}H_{29}IN_7O_6S_2$ 738.6 (M+H); found: 738.1. $^1$H NMR (300 MHz, $CD_3OD$) δ 8.22–8.18 (m, 1H), 8.13–8.08 (m, 1H), 7.84 (dd, J=1.21 and 7.98 Hz, 1H), 7.69–7.58 (2H), 7.49 (dd, J=1.67 and 7.75 Hz, 1H), 7.38–7.30 (m, 2H), 7.01 (dt, J=1.72 and 7.83 Hz, 1H), 6.18 (dd, J=0.78 and 7.65 Hz, 1H), 5.93 (dd, J=3.89 and 10.03 Hz, 1H), 5.03 (d, J=16.35 Hz, 1H), 4.85 (d, J=16.41 Hz, 1H), 4.66 (s, 2H), 4.20–4.07 (m, 2H), 2.69–2.58 (m, 1H), 2.31 (s, 3H), 2.15–2.03 (m, 1H).

EXAMPLE 3

N-{(1S)-1-[2-(Amidinoaminooxy)ethyl]-2-oxo-2-(1,3-thiazol-2-yl)ethyl}-2-(3-{[(3-iodophettyl)sulfonyl]amino}-6-methyl-2-oxohydropyridyl)acetamide

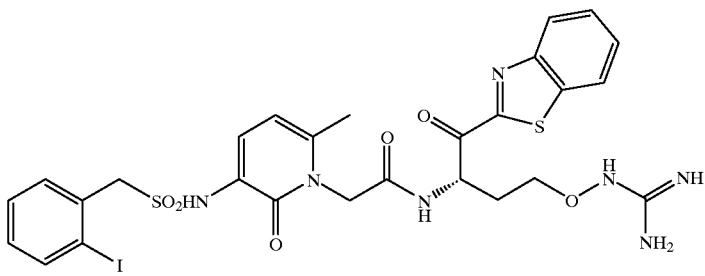

The title compound was prepared from N-{(1S)-2-benzothiazol-2-yl-1-[2-({[tert-butoxy)carbonylamino]iminomethyl}aminooxy)ethyl]-2-oxoethyl}-2-[3-({[(2-iodophenyl)methyl]sulfonyl}amino)-6-methyl-2-

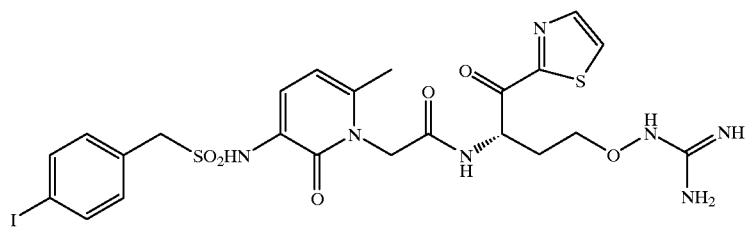

1. 3-Iodobenzenesulfonic Acid (Noronha, O.P.D., J. Labelled Compounds, IX: 261 (1973))

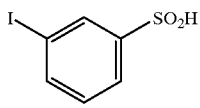

To a 3-neck flask charged with concentrated HCl (40 mL) was added metanilic acid (11.2 g, 64.7 mmol) and stirred at room temperature for 5 minutes. The suspension was then cooled in an ice-salt bath to 0–5° C. A solution of NaNO$_2$ (4.9 g, 71.1 mmol) in H$_2$O (10 mL) was added. The temperature was controlled at 0–5° C. After 15 minutes, pre-cooled solution of KI (10.7 g, 64.7 mmol) in H$_2$O (12 mL) was added, and the reaction mixture was stirred over night to give a brown suspension. The suspension was concentrated to a volume of about 50 mL under reduced pressure. After cooling to room temperature, the solid was filtered, washed with cold H$_2$O (3 mL), and recrystallized from hot water to give the title compound (5.7 g, 31% yield) as a pale yellow powder. Mass spectrum (LCMS, ESI) calcd. for C$_6$H$_6$IO$_3$S 284.1 (M); found: 284.1. $^1$H NMR (300 MHz, DMSO-d-6) δ 7.92 (t, J=1.59 Hz, 1H), 7.69 (ddd, J=1.13, 1.79, and 7.74 Hz, 1H), 7.61 (dt, J=1.49 and 7.71 Hz, 1H), 7.16 (t, J=7.79 Hz, 1H).

2. tert-Butyl 2-(3-{[(3-Iodophenyl)sulfonyl]amino}-6-methyl-2-oxohydropyridyl)acetate

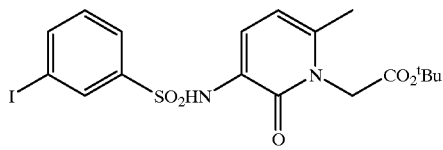

To a flask charged with 3-iodobenzenesulfonic acid (853 mg, 3.0 mmol), as prepared in the preceding step, was added phosphorus oxychloride (8 mL) and heated at 130° C. for 3 h. The mixture was then cooled to room temperature and poured into an ice-water slash (150 mL), where upon 3-iodobenzenesulfonyl chloride separated out as an oil sitting on the bottom of the ice-water. The product was taken up into toluene (2×150 mL). Organic extracts were combined, washed with brine, concentrated to about 6 mL, and diluted with DCM (4.0 mL). To this 3-iodobenzenesulfonyl chloride solution was then added a solution of 3-amino-6-methyl-1-(tert-butyloxycarbonylmethyl)-2-pyridinone (543 mg, 2.3 mmol), as prepared in step 3 of Example 1, in DCM (4.0 mL), and triethylamine (0.4 mL). After 16 hours stirring at room temperature, the mixture was diluted with DCM (100 mL) and partitioned between DCM and H$_2$O (30 mL). The aqueous layer was separated and back extracted with DCM (2×60 mL). Organic layers were combined and washed with saturated NaHCO$_3$ (2×30 mL), 10% KHSO$_4$ (2×30 mL), brine (30 mL), dried over MgSO$_4$, and concentrated to give crude product as a brown solid. The solid was washed with EtOAc/hexane (1:2, 2×10 mL) and ether (10 mL) to deliver the title compound (1.07 g, 93% yield) as a pale brown powder. Mass spectrum (LCMS, ESI) calcd. for C$_{18}$H$_{21}$IN$_2$O$_5$S 504.3 (M+H); found: 504.3. $^1$H NMR (300 MHz, CD$_3$OD) δ 8.16 (t, J=1.66 Hz, 1H), 7.86–7.83 (m, 1H), 7.79 (ddd, J=1.08, 1.78, and 8.04 Hz, 1H), 7.68 (s, 1H), 7.44 (d, J=7.58 Hz, 1H), 7.17 (t, J=7.88 Hz, 1H), 6.05 (dd, J=0.77 and 7.61 Hz, 1H), 4.66 (s, 2H), 2.23 (s, 3H), 1.43 (s, 9H).

3. 2-(3-{[(3-Iodophenyl)sulfonly]amino}-6-methyl-2-oxohydropyridyl)acetic Acid

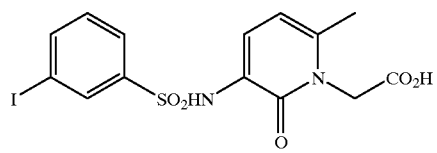

The title compound was prepared from tert-butyl 2-(3-{[(3-iodophenyl)sulfonyl]amino}-6-methyl-2-oxohydropyridyl)acetate, as prepared in the preceding step, using the same experimental procedure in step 5 of Example 1. Mass spectrum (LCMS, ESI) calcd. for C$_{20}$H$_{32}$IN$_5$O$_7$S 454.2 (M+H), found: 454.0.

4. (2S)-4-({[(tert-Butoxy)carbonylamino]iminomethyl}aminooxy)-2-[2-(3-{[(3-iodophenyl)sulfonyl]amino}-6-methyl-2-oxohydropyridyl)acetylamino]-N-methoxy-N-methylbutanamide

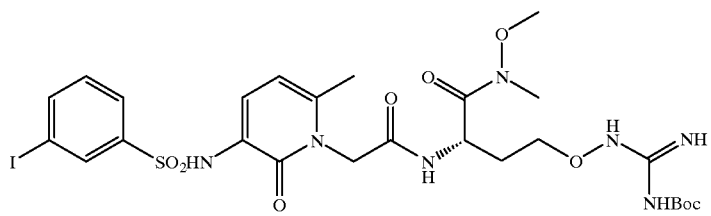

To 2-(3-{[(3-Iodophenyl)sulfonyl]amino}-6-methyl-2-oxohydropyridyl) acetic acid (127 mg, 0.283 mmol), as prepared in the preceding step, in DMF (1.0 mL) was added BOP (138 mg, 0.321 mmol), a solution of (2S)-2-amino-4-({[(tert-butoxy)carbonylamino]iminomethyl}aminooxy)-N-methoxy-N-methylbutanamide (90 mg, 0.283 mmol), as prepared in step 8 of Example 1, and DIEA (256 mg, 1.98 mmol) in DMF (0.4 mL). After stirring at room temperature for 24 h, solvents were removed, the residue was partitioned between Et$_2$O (200 mL) and H$_2$O (50 mL), and the aqueous layer was back extracted with EtOAc (100 mL). Organic layers were combined and washed with saturated NaHCO$_3$ (2× 40 mL), H$_2$O (40 mL), NaHSO$_4$ (10%, 2×40 mL), H$_2$O (40 mL), brine (40 mL), dried over Na$_2$SO$_4$, concentrated, and flash chromatographed on silica gel, eluting with MeOH/DCM (0, 2.5, and 5%) to give desired amide 31 (176 mg, 83% yield) as an oil. Mass spectrum (LCMS, ESI) calcd. for $C_{26}H_{36}IN_7O_9S$ 749.6 (M+H); found: 749.8. $^1$H NMR (300 MHz, $CD_3OD$) δ 8.14 (t, J=1.68 Hz, 1H), 7.90 (ddd, J=1.06, 1.63, and 7.89 Hz, 1H), 7.80 (ddd, J=0.95, 1.74, and 7.92 Hz, 1H), 7.48 (d, 7.61 Hz, 1H), 7.23 (t, J=7.91 Hz, 1H), 6.16 (dd, J=0.71 and 7.65 Hz, 1H), 5.04–4.95 (m, 1H), 4.85 (d, J=16.35 Hz, 1H), 4.70 (d, J=16.35 Hz, 1H), 3.87 (dd, J=4.61 and 6.41 Hz, 2H), 3.75 (s, 3H), 3.18 (s, 3H), 2.27 (s, 3H), 2.21–2.10 (m, 1H), 1.84–1.74 (m, 1H), 1.48 (s, 9H).

5. N-{(1S)-1-[2-(Amidinoaminooxy)ethyl]-2-oxo-2-(1,3-thiazol-2-yl)ethyl}-2-(3-{[(3-iodophenyl)sulfonyl]amino}-6-methyl-2-oxohydropyridyl)acetamide

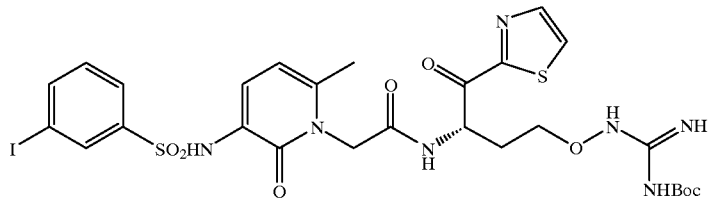

The title compound was prepared by coupling of (2S)-4-({[(tert-butoxy)carbonylamino]iminomethyl}aminooxy)-2-[2-(3-{[(3-iodophenyl) sulfonyl]amino}-6-methyl-2-oxohydropyridyl)acetylamino]-N-methoxy-N-methylbutanamide, as prepared in the preceding step, with lithiated thiazole under the same conditions as in step 10 of Example 1. Mass spectrum (LCMS, ESI) calcd. for $C_{27}H_{32}IN_7O_8S_2$ 773.6 (M+H); found: 773.8. $^1$H NMR (300 MHz, $CD_3OD$) δ 8.13 (t, J=1.66 Hz, 1H), 8.06 (d, J=3.03 Hz, 1H), 7.99 (d, J=3.11 Hz, 1H), 7.88 (ddd, J=0.97, 1.58, and 7.87 Hz, 1H), 7.78 (ddd, J=1.08, 1.77, and 7.92 Hz, 1H), 7.47 (d, J=7.60 Hz, 1H), 7.21 (t, J=7.89 Hz, 1H), 6.16 (dd, J=0.80 and 7.64 Hz, 1H), 5.68 (dd, J=4.34 and 8.79 Hz, 1H), 4.88 (d, J=16.36 Hz, 1H), 4.74 (d, J=16.35 Hz, 1H), 3.96–3.86 (m, 2H), 2.43–2.33 (m, 1H), 2.26 (s, 3H), 2.12–2.02 (m, 1H), 1.48 (s, 9H).

6. N-{(1S)-1-[2-(Amidinoaminooxy)ethyl]-2-oxo-2-(1,3-thiazol-2-yl)ethyl}-2-(3-{[(3-iodophenyl)sulfonyl]amino}-6-methyl-2oxohydropyridyl)acetamnide ethyl]-2-oxo-2-(1,3-thiazol-2-yl)ethyl}2-(3-{[(3-iodophenyl)sulfonyl]amino}-6-methyl-2-oxohydropyridyl)acetamide, as prepared in the preceding step, under the same conditions as in step 11 of Example 1. Mass spectrum (LCMS, ESI) calcd. for $C_{27}H_{32}IN_7O_8S_2$ 773.6 (M+H); found: 773.8. $^1$H NMR (300 MHz, $CD_3OD$) δ 8.14 (t, J 1.72 Hz, 1H), 8.10 (d, J=3.06 Hz, 1H), 8.06 (d, J=2.97 Hz, 1H), 7.91 (td, J=1.31 and 7.91 Hz, 1H), 7.77 (ddd, J=0.97, 1.70, and 7.92 Hz, 1H), 7.48 (d, J=7.62 Hz, 1H), 7.23 (t, J=7.91 Hz, 1H), 6.21 (dd, J=0.49 and 7.65 Hz, 1H), 5.77 (dd, J=3.76 and 10.04 Hz, 1H), 4.88 (d, J=16.23 Hz, 1H), 4.71 (dd, J=1.14 and 16.28 Hz, 1H), 4.11–3.99 (m, 1H), 2.28 (s, 3H), 2.05–1.93 (m, 1H).

EXAMPLE 4

N-{(1S)-1-[2-(Amidinoaminooxy)ethyl]-2-benzothiazol-2-yl-2-oxoethyl}-2-(3-{[(3-iodopheityl)sulfonyl]amino}-6-methyl-2-oxohydropyridyl)acetamide

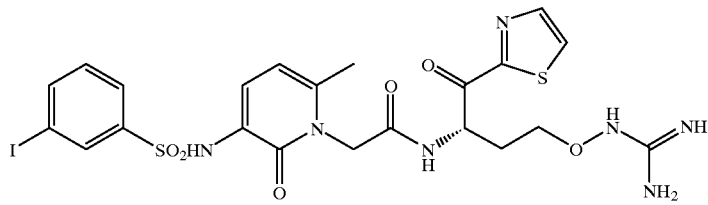

The title compound was prepared by removing the Boc protecting group from N-{(1S)-1-[2-(amidinoaminooxy)

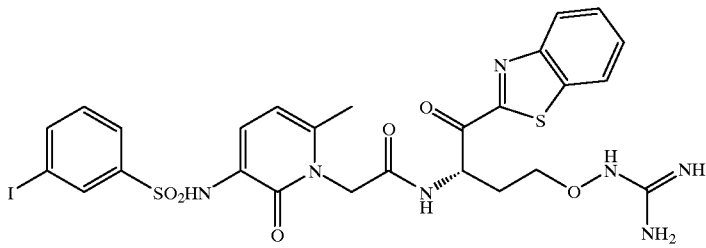

1. N-{(1S)-2-Benzothiazol-2-yl-1-[2-({[(tert-butoxy)carbonylamino]iminomethyl)aminooxy)ethyl}-2-oxoethyl}-2-(3-{[(3-iodophenyl) sulfonyl]amino}-6-methyl-2-oxohydropyridyl)acetamide

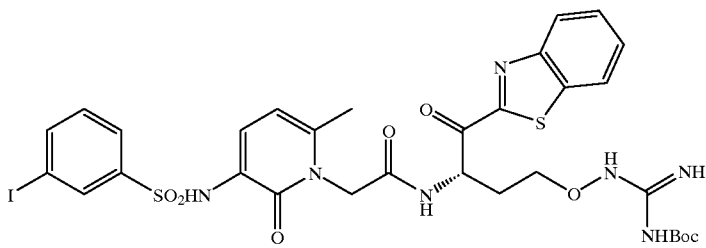

The title compound was prepared by coupling of (2S)-4-({[(tert-butoxy)carbonylamino]iminomethyl}aminooxy)-2-[2-(3-{[(3-iodophenyl)sulfonyl]amino}6-methyl-2-oxohydropyridyl)acetylamino]-N-methoxy-N-methylbutanamide, as prepared in step 4 of Example 3, with lithiated benzothiazole under the same conditions as in step 10 of Example 1. Mass spectrum (LCMS, ESI) calcd. for $C_{31}H_{34}IN_7O_8S_2$ 823.7 (M+H); found: 823.9. $^1$H NMR (300 MHz, $CD_3OD$) 68.21–8.15 (m, 1H), 8.12–8.05 (m, 1H), 7.69–7.83 (m, 1H), 7.80–7.75 (m, 1H), 7.63–7.54 (m, 2H), 7.51–7.43 (m, 1H), 7.19 (t, J=7.91 Hz, 1H), 6.14 (d, J=7.67 Hz, 1H), 5.81 (dd, J=4.33 and 8.79 Hz, 1H), 4.90 (d, J=16.38 Hz, 1H), 4.76 (d, J=16.38 Hz, 1H), 4.00–3.95 (m, 2H), 2.52–2.41 (m, 1H), 2.26 (s, 3H), 2.12–2.05 (m, 1H), 1.47 (s, 9H).

2. N-{(1S)-1-[2-Amiditioaminooxy)ethyl]-2-benzothiazol-2-yl-2-oxoethyl}-2-(3-{[(3-iodophenyl)sulfonyl]amino}-6-methyl-2-oxohydropyridyl)acetamide

The title compound was prepared by removing the Boc group from N-{(1S)-2-benzothiazol-2-yl-1-[2-({[(tert-butoxy)carbonylamino]iminomethyl}aminooxy)ethyl]-2-oxoethyl}-2-(3-{[(3-iodophenyl)sulfonyl]amino}-6-methyl-2-oxohydropyridyl) acetamide, as prepared in the preceding step, under the same conditions as in step 11 of Example 1. Mass spectrum (LCMS, ESI) calcd. for $C_{27}H_{31}IN_7O_6S_2$ 724.6 (M+H); found: 724.0. $^1$H NMR (300 MHz, $CD_3OD$) δ 8.21–8.18 (m, 1H), 8.13–8.10 (2H), 7.89 (ddd, J=0.97, 1.70, and 7.91 Hz, 1H), 7.76 (ddd, J=0.93, 1.76, and 7.92 Hz, 1H), 7.67–7.59 (2H), 7.47 (d, J=7.61 Hz, 1H), 7.21 (t, J=7.91 Hz, 1H), 6.19 (dd, J=0.75 and 7.65 Hz, 1H), 5.88 (dd, J=3.88 and 9.93 Hz, 1H), 4.90 (d, J=16.40 Hz, 1H), 4.74 (d, 16.40 Hz, 1H), 4.15–4.05 (2H), 2.65–2.54 (m, 1H), 2.26 (s, 3H), 2.21–2.01 (m, 1H).

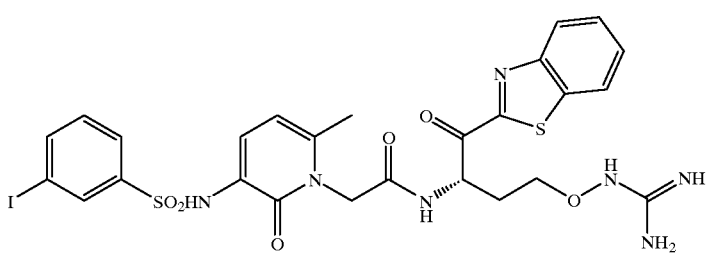

EXAMPLE 5

(2S)-4-(Amidinoaminooxy)-2-[2-(3-{[(3-iodophenyl)sulfonyl]amino}-6-methyl-2-oxohydropyridyl)acetylamino]-N-methoxy-N-methylbutanamide

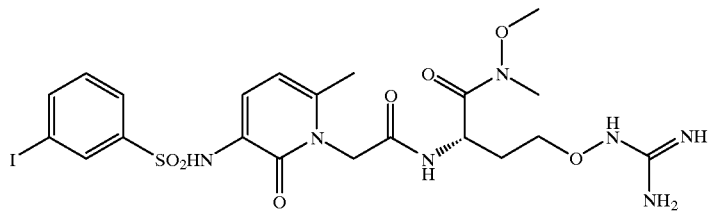

The title compound was prepared by removing the Boc group from (2S)-4-({[(tert-butoxy)carbonylamino]iminomethyl}aminooxy)-2-[2-(3-{[(3-iodophenyl)sulfonyl]amino}-6-methyl-2-oxohydropyridyl)acetylamino]-N-methoxy-N-methylbutanamide, as prepared in step 4 of Example 3, under the same condition as in step 11 of Example 1. Mass spectrum (LCMS, ESI) calcd. for $C_{21}H_{29}IN_7O_7S$ 450.5 (M+H); found: 450.1. $^1$H NMR (300 MHz, $CD_3OD$) δ 8.15 (t, J=1.63 Hz, 1H), 7.93 (ddd, J=0.87, 1.38, and 7.93 Hz, 1H), 7.79 (ddd, J=1.04, 1.64, and 7.90 Hz, 1H), 7.48 (d, J=7.63 Hz, 1H), 7.24 (t, J=7.91 Hz, 1H), 6.21 (d, J=8.04 Hz, 1H), 5.09–5.07 (m, 1H), 4.83 (d, J=16.41 Hz, 1H) 4.69 (d, J=16.41 Hz, 1H), 3.98 (dd, J=5.06 and 6.60 Hz, 2H), 3.77 (s, 3H) 3.21 (s, 3H), 2.29 (s, 3H), 2.24–2.13 (m, 1H), 1.99–1.84 (m, 1H).

EXAMPLE 6

Tablet Preparation

Tablets containing 25.0, 50.0, and 100.0 mg, respectively, of the following active compounds are prepared as illustrated below:

a. N-{(1 S)-1-[2-(Amidinoaminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide; and b. N-{(1S)-1-[2-(Amidinoaminooxy)ethyl]-2-benzothiazol-2-yl-2-oxoethyl}-2-[3-({[(2-iodophenyl)methyl]sulfonyl]amino}-6-methyl-2-oxohydropyridyl]acetamide Tablet for Doses Containing From 25–100 Mg of the Active Compound

|  | Amount-mg | | |
| --- | --- | --- | --- |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 7

Intravenous Solution Preparation

An intravenous dosage form of the above-indicated active compounds is prepared as follows:

| Active Compound | 0.5–10.0 mg |
| --- | --- |
| Sodium Citrate | 5–50 mg |

-continued

| Citric Acid | 1–15 mg |
| --- | --- |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 8

In vitro Inhibition of Purified Enzymes

Reagents: All buffer salts were obtained from Sigma Chemical Company (St. Louis, Mo.), and were of the highest purity available. The enzyme substrate N-benzoyl-Ile-Glu-Gly-Arg-p-nitroanilide hydrochloride (Sigma B2291) was obtained from Sigma. N-succinyl-Ala-Ala-Pro-Arg-p-nitroanilide (BACHEM L-1720) was obtained from BACHEM (King of Prussia, Pa.). Human α-thrombin and human factor Xa were obtained from Enzyme Research Laboratories (South Bend, Indiana).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determnination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human α-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 mM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 mM.

The results of compounds of the invention are shown in the following table.

TABLE 1

Biological activity data

| Example | Factor Xa % inhibition @ conc. (μM) | Human Thrombin $K_i$ (nM) |
|---|---|---|
| 1 | 16% @ 20 | 14 |
| 2 | 51% @ 13 | 75 |
| 3 | | 45 |
| 4 | | 17 |

The results indicate that the compounds of the present invention are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

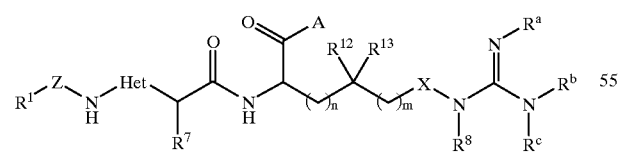

I or a solvate, hydrate or pharmaceutically acceptable salt thereof; wherein:

$R^1$ is $C_{6-10}$ar($C_{1-4}$)alkyl, $C_{6-10}$aryl, $C_{4-7}$cycloalkyl($C_{1-4}$) alkyl, heterocycle or heterocyclo($C_{1-4}$)alkyl, any of which is optionally substituted; and wherein the heterocycle of said heterocycle or said heterocyclo($C_{1-4}$) alkyl is a 5- to 7-membered mono-cyclic or a 9- to 10-membered bi-cyclic heterocyclic ring that is saturated or unsaturated, and contains 1 to 3 heteratoms selected from N, O and S;

Z is —$SO_2$—, —OCO—, —CO—, —$NR^2CO$— or a covalent bond, where $R^2$ is hydrogen, alkyl, aralkyl, aryl, hydroxy($C_{2-10}$)alkyl, amino($C_{2-10}$)alkyl, monoalkylamino($C_{2-10}$)alkyl, dialkylamino($C_{2-10}$) alkyl or carboxyalkyl;

Het is selected from the group consisting of

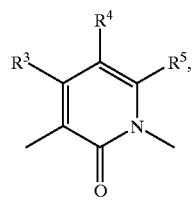

where $R^3$, $R^4$ and $R^5$ are independently hydrogen, $C_{1-4}$alkyl, $C_{3-7}$cycloalkyl, $C_{6-14}$aryl, $C_{6-10}$ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl or cycloalkoxycarbonyl;

$R^7$ is hydrogen, $C_{1-4}$alkyl, or $C_{2-4}$alkenyl;

$R^8$ is hydrogen, $C_{1-6}$alkyl, $C_{2-6}$alkenyl, $C_{6-10}$ar($C_{1-6}$) alkyl, $C_{6-10}$aryl, hydroxyalkyl, aminoalkyl, monoalkylamino($C_{2-10}$)alkyl, dialkylamino($C_{2-10}$) alkyl or carboxyalkyl;

$R^{12}$ and $R^{13}$ are independently hydrogen, $C_{1-4}$alkyl, $C_{6-10}$ar($C_{1-6}$)alkyl, $C_{6-10}$aryl, hydroxyalkyl, aminoalkyl, monoalkylamino($C_{2-10}$)alkyl, dialkylamino($C_{2-10}$)alkyl or carboxyalkyl; or $R^{12}$ and $R^{13}$ are taken together to form —$(CH_2)_y$—, where y is 2 to 7;

X is oxygen or $NR^9$, where $R^9$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

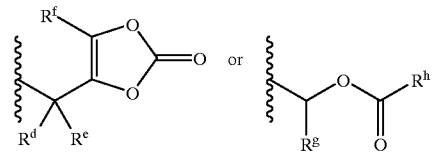

where $R^d$ and $R^e$ are independently hydrogen, $C_{1-6}$alkyl, $C_{2-6}$alkenyl or phenyl, $R^f$ is hydrogen, $C_{1-6}$alkyl, $C_{2-6}$alkenyl or phenyl, $R^g$ is hydrogen, $C_{1-6}$alkyl, $C_{2-6}$alkenyl or phenyl, and $R^h$ is aralkyl or $C_{1-6}$alkyl;

A is selected from the group consisting of:

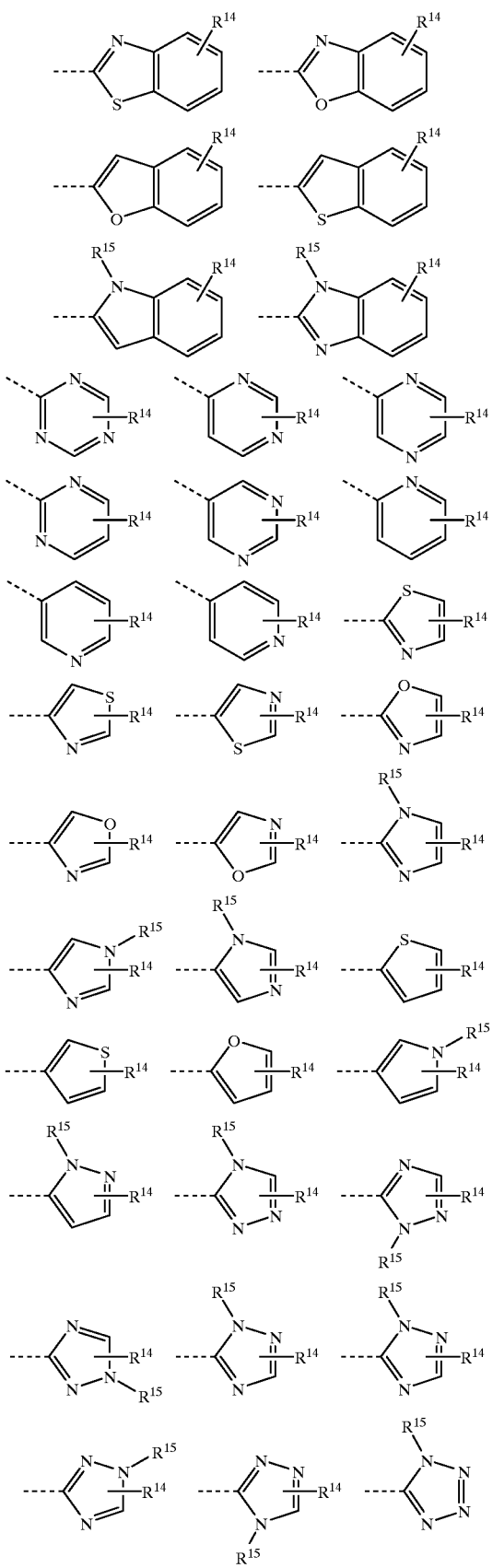

and —N(CH$_3$)—O—CH$_3$, where

R$^{14}$ is hydrogen, C$_{1-6}$alkyl, carboxy(C$_{1-6}$)alkyl, carboxy, C$_{6-20}$aralkyl, C$_{3-7}$cycloalkyl, C$_{1-16}$alkoxycarbonyl, C$_{1-16}$alkoxycarbonyl (C$_{1-16}$)alkyl, or (C$_{6-10}$)aryl;

R$^{15}$ is hydrogen, C$_{3-7}$cycloalkyl, or C$_{1-4}$alkyl; and the dashed line indicates point of attachment;

n is from zero to 8; and m is from zero to 6.

2. A compound of claim 1, wherein R$^1$ is C$_{6-10}$ar(C$_{1-14}$) alkyl, C$_{6-10}$aryl, C$_{4-7}$cycloalkyl (C$_{1-4}$)alkyl, any of which is optionally substituted by 1–5 substituents independently selected from the group consisting of hydroxy, nitro, trifluoromethyl, halogen, C$_{1-6}$alkyl, C$_{2-16}$alkenyl, C$_{6-10}$aryl, C$_{1-6}$alkoxy, C$_{6-10}$ar(C$_{1-6}$)alkoxy, amino(C$_{1-6}$)alkyl, amino (C$_{1-6}$)alkoxy, amino, mono(C$_{1-4}$)alkylamino, di(C$_{1-4}$) alkylamino, C$_{2-6}$alkylcarbonylamino, C$_{2-6}$alkoxycarbonylamino, C$_{2-6}$alkoxycarbonyl, carboxy, hydroxy(C$_{1-6}$)alkyl, hydroxy(C$_{2-6}$)alkoxy, (C$_{1-6}$)alkoxy(C$_{2-6}$)alkoxy, mono- and di-C$_{14}$alkylamino(C$_{2-6}$)alkoxy, C$_{2-10}$mono(carboxyalkyl)amino, bis(C$_{2-10}$carboxyalkyl) amino, C$_{6-14}$ar(C$_{1-6}$)alkoxycarbonyl, C$_{2-6}$alkynylcarbonyl, C$_{1-6}$alkylsulfonyl, C$_{2-6}$alkenylsulfonyl, C$_{2-6}$alkynylsulfonyl, C$_{6-10}$arylsulfonyl, C$_{6-10}$ar(C$_{1-6}$) alkylsulfonyl, C$_{1-6}$alkylsulfonyl, C$_{1-6}$alkylsulfonamido, C$_{6-10}$arylsulfonamido, C$_{6-10}$ar(C$_{1-6}$)alkylsulfonamido, amidino, guanidino, C$_{1-6}$alkyliminoamino, formyliminoamino, C$_{2-6}$carboxyalkoxy, C$_{2-6}$carboxyalkyl, C$_{2-6}$carboxyalkylamino, cyano, trifluoromethoxy, and perfluoroethoxy.

3. A compound of claim 1, wherein R$^1$ is benzyl, fluorobenzyl, chlorobenzyl, iodobenzyl, dichlorobenzyl, bromobenzyl, trifluoromethylbenzyl, methylsulfonylbenzyl, di(trifluoromethyl)benzyl, methylbenzyl, t-butylbenzyl, methoxybenzyl, dimethoxybenzyl, hydroxybenzyl, carboxybenzyl, amninobenzyl, methylaminobenzyl, n-butylaminobenzyl, amidinobenzyl, guanidinobenzyl, formyliminoaminobenzyl, acetimidoylaminobenzyl, methoxycarbonylbenzyl, ethoxycarbonylbenzyl, carboxymethoxybenzyl, naphthylmethyl, hydroxynaphthylmethyl, cyclohexylmethyl, cyclopentylmethyl, phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, or cyclopentyl.

4. A compound of claim 1, wherein R$^1$ is phenyl, 2-chlorophenyl, 3-chlorophenyl, 4-chlorophenyl, 4-bromophenyl, 3-iodophenyl, 4-iodophenyl, 4-methoxyphenyl, 4-methylphenyl, 2-trifluoromethylphenyl, 4-trifluoromethylphenyl, 2-fluorophenyl, 3-fluorophenyl, 4-fluorophenyl, 3,4-dichlorophenyl, 3-chloro-4-fluorophenyl, 3,5-dichlorophenyl, 2-methylphenyl, 3-methylphenyl, 4-ethylphenyl, 2-methylsulfonylphenyl, 4-isopropylphenyl, 3,4-dimethoxyphenyl, 2,4,6-trimethylphenyl, 2,5-dimethylphenyl, 4-vinylphenyl, 2-chloro-6-methylphenyl, 3-bromo-6-methoxyphenyl, 3-chloro-2-methylphenyl, 2-chloro-5-trifluoromethylphenyl, 2,4-dichlorophenyl, 2-butoxy-5-(1,1-dimethylpropyl)phenyl, 3-nitrophenyl, 4-chloro-3-nitrophenyl, 4-methylcarbonylaminophenyl, 4-tert-butylphenyl, 3-cyanophenyl, 4-methylsulfonylphenyl, pentafluorophenyl, 2,5-dichlorophenyl, 2,4-dimethoxyphenyl, 2-methyl-5-nitrophenyl, 3-chloro-2-cyanophenoxy)phenyl, 2-chloro-4-fluorophenyl, 3-chloro-6-methoxyphenyl, 2-methoxy-5-methylphenyl, 4-phenylphenyl, 2-propylbutyl, 5-chloro-2-methoxyphenyl, 2-cyanophenyl, 2-(N-hydroxy)aminophenyl, 2-(4-biphenylmethoxy)phenyl, 2-(3-biphenylmethoxy)phenyl, benzyl, 2-(phenylsulfonyl)phenyl, 2,4-bis(methylsulfonyl)phenyl, 2-chloro-4-methylsulfonylphenyl, benzyl, 3-chlorobenzyl, 3-trifluoromethylbenzyl, 2-trifluoromethylbenzyl, 2-iodobenzyl, 2-chlorobenzyl, 2-bromobenzyl, 3-iodobenzyl, 3-fluorobenzyl, 4-chlorobenzyl, 2-chloro-6-fluorobenzyl, 2-fluorobenzyl, 2,3-dichlorobenzyl, 3,4-difluorobenzyl, 2,4-dichlorobenzyl, 2,5-dichlorobenzyl, 3,4-dichlorobenzyl, 2-methylbenzyl, 5-chloro-2-methoxybenzyl, 2-cyanobenzyl, 2-(4-biphenylmethoxy)benzyl, 2-(3-biphenylmethoxy)benzyl, 2-(phenylsulfonyl)benzyl, 2,4-bis(methylsulfonyl)benzyl, 3-methylsulfonylbenzyl, 2-chloro-4-methylsulfonylbenzyl, 1-naphthalenylmethyl, 2-naphthalenylmethyl, or 2-naphthalenyl.

5. A compound of claim 1, wherein $R^1$ is 2-iodophenyl, 3-iodophenyl, 4-iodophenyl, 2-iodobenzyl, 3-iodobenzyl, or 4-iodobenzyl.

6. compound of claim 1, wherein Z is —$SO_2$— or a covalent bond.

7. A compound of claim 1, wherein $R^3$, $R^4$ and $R^5$ are independently hydrogen, methyl, ethyl, propyl, chloro, bromo, trifluoromethyl, hydroxymethyl, carboxamide, nitro, phenyl, cyclopropyl, isopropyl, methoxycarbonyl, ethoxycarbonyl or benzyl.

8. A compound of claim 1, wherein $R^3$ and $R^4$ are independently hydrogen, $C_{1-12}$alkyl, or $C_{2-6}$alkenyl.

9. A compound of claim 8, wherein $R^3$ and $R^4$ are hydrogen.

10. A compound of claim 1, wherein $R^5$ is hydrogen, halogen, $C_{1-5}$alkyl, $C_{3-6}$alkenyl, $C_{3-5}$cycloalkyl, trifluoromethyl, or $C_{1-4}$alkoxy.

11. A compound of claim 1, wherein Het is:

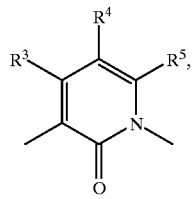

where:
$R^3$ and $R^4$ are independently hydrogen or methyl; and
$R^5$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrolyl, 3-pyrolyl, 1-hexyl, S-2-hexyl, R-2-hexyl, R-3-hexyl, and S-3-hexyl.

12. A compound of claim 10, wherein $R^5$ is hydrogen, methyl, ethyl, propyl or isopropyl.

13. A compound of claim 1, wherein $R^7$ is hydrogen.

14. A compound of claim 1, wherein A is:

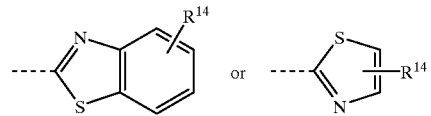

wherein $R^{14}$ is H or $C_{1-4}$alkyl.

15. A compound of claim 14, wherein $R^{14}$ is hydrogen.

16. A compound of claim 1, wherein $R^8$ is hydrogen, $C_{1-6}$alkyl or $C_{6-10}$aryl($C_{1-6}$)alkyl.

17. A compound of claim 1, wherein X is oxygen.

18. A compound of claim 1, wherein X is $NR^9$, where $R^9$ is hydrogen or $C_{1-6}$alkyl, optionally substituted by one, two or three substituents independently selected from the group consisting of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl and imidazolyl.

19. A compound of claim 1, wherein $R^{12}$ and $R^{13}$ are independently hydrogen, $C_{1-6}$alkyl, $C_{6-10}$ar($C_{1-6}$)alkyl, $C_{6-10}$aryl, hydroxy($C_{2-10}$)alkyl or $C_{2-7}$carboxyalkyl.

20. A compound of claim 19, wherein $R^{12}$ and $R^{13}$ are independently hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl or 4-carboxypropyl.

21. A compound of claim 1, wherein $R^a$, $R^b$ and $R^c$ are independently hydrogen, hydroxy, $C_{1-6}$alkyl, $C_{1-6}$alkoxy, cyano or —$CO_2R^w$, where $R^w$, in each instance, is $C_{1-4}$alkyl, $C_{4-7}$cycloalkyl or benzyloxycarbonyl.

22. A compound of claim 21, wherein $R^a$, $R^b$ and $R^c$ are independently hydrogen, methyl, ethyl, propyl, n-butyl, hydroxy, methoxy, ethoxy, cyano, —$CO_2CH_3$, —$CO_2CH_2CH_3$ or —$CO_2CH_2CH_2CH_3$.

23. A compound of claim 21, wherein $R^a$, $R^b$ and $R^c$ are each hydrogen.

24. A compound of claim 1, wherein n is from zero to 4, and m is from zero to 4.

25. A compound of claim 24, wherein n is zero or 1, and m is zero or 1.

26. A compound of claim 1, wherein Z is —$SO_2$—; $R^1$ is substituted or unsubstituted aryl or aralkyl; Het is

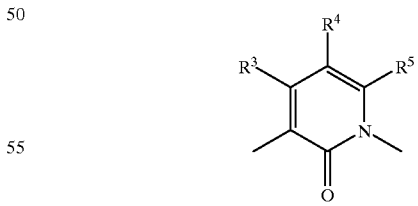

where $R^3$ and $R^4$ are each hydrogen and $R^5$ is methyl; A is as defined in claim 1; $R^{12}$ and $R^{13}$ are both hydrogen; X is O; $R^8$ is hydrogen, $C_{1-6}$alkyl or $C_{6-10}$aryl($C_{1-6}$)alkyl; and $R^a$, $R^b$ and $R^c$ are independently hydrogen, hydroxy, $C_{1-6}$alkyl, or $C_{1-6}$alkoxy.

27. A compound of claim 26, wherein:
$R^1$ is substituted or unsubstituted benzyl or substituted or unsubstituted phenyl;

A is

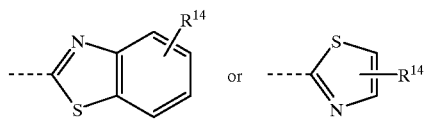

wherein $R^{14}$ is H or $C_{1-4}$alkyl; and
$R^a$, $R^b$ and $R^c$ are all hydrogen.

28. A compound of claim 27, wherein $R^1$ is phenyl, 2-chlorophenyl, 3-chlorophenyl, 4-chlorophenyl, 4-bromophenyl, 3-iodophenyl, 4-iodophenyl, 4-methoxyphenyl, 4-methylphenyl, 2-trifluoromethylphenyl, 4-trifluoromethylphenyl, 2-fluorophenyl, 3-fluorophenyl, 4-fluorophenyl, 3,4-dichlorophenyl, 3-chloro-4-fluorophenyl, 3,5-dichlorophenyl, 2-methylphenyl, 3-methylphenyl, 4-ethylphenyl, 2-methylsulfonylphenyl, 4-isopropylphenyl, 3,4-dimethoxyphenyl, 2,4,6-trimethylphenyl, 2,5-dimethylphenyl, 4-vinylphenyl, 2-chloro-6-methylphenyl, 3-bromo-6-methoxyphenyl, 3-chloro-2-methylphenyl, 2-chloro-5-trifluoromethylphenyl, 2,4-dichlorophenyl, 2-butoxy-5-(1,1-dimethylpropyl)phenyl, 3-nitrophenyl, 4-chloro-3-nitrophenyl, 4-methylcarbonylaminophenyl, 4-tert-butylphenyl, 3-cyanophenyl, 4-methylsulfonylphenyl, pentafluorophenyl, 2,5-dichlorophenyl, 2,4-dimethoxyphenyl, 2-methyl-5-nitrophenyl, 3-chloro-2-cyanophenoxy)phenyl, 2-chloro-4-fluorophenyl, 3-chloro-6-methoxyphenyl, 2-methoxy-5-methylphenyl, 4-phenylphenyl, 2-propylbutyl, 5-chloro-2-methoxyphenyl, 2-cyanophenyl, 2-(N-hydroxy)aminophenyl, 2-(4-biphenylmethoxy)phenyl, 2-(3-biphenylmethoxy)phenyl, benzyl, 2-(phenylsulfonyl)phenyl, 2,4-bis(methylsulfonyl)phenyl, 2-chloro-4-methylsulfonylphenyl, benzyl, 3-chlorobenzyl, 3-trifluoromethylbenzyl, 2-trifluoromethylbenzyl, 2-iodobenzyl, 2-chlorobenzyl, 2-bromobenzyl, 3-iodobenzyl, 3-fluorobenzyl, 4-chlorobenzyl, 2-chloro-6-fluorobenzyl, 2-fluorobenzyl, 2,3-dichlorobenzyl, 3,4-difluorobenzyl, 2,4-dichlorobenzyl, 2,5-dichlorobenzyl, 3,4-dichlorobenzyl, 2-methylbenzyl, 5-chloro-2-methoxybenzyl, 2-cyanobenzyl, 2-(4-biphenylmethoxy)benzyl, 2-(3-biphenylmethoxy)benzyl, 2-(phenylsulfonyl)benzyl, 2,4-bis(methylsulfonyl)benzyl, 3-methylsulfonylbenzyl, 2-chloro-4-methylsulfonylbenzyl, 1-naphthalenylmethyl, 2-naphthalenylmethyl, or 2-naphthalenyl.

29. A compound of claim 1, which is one of:

N-{(1S)-1-[2-(Amidinoaminooxy)ethyl]-2-oxo-2-(1,3-thiazol-2-yl)ethyl}-2-[3-({[(2-iodophenyl)methyl]sulfonyl}amino)-6-methyl-2-oxohydropyridyl]acetamide;

N-{(1S)-1-[2-(Amidinoaminooxy)ethyl]-2-benzothiazol-2-yl-2-oxoethyl}-2-[3-({[(2-iodophenyl)methyl]sulfonyl}amino)-6-methyl-2-oxohydropyridyl]acetamide;

N-{(1S)-1-[2-(Amidinoaminooxy)ethyl]-2-oxo-2-(1,3-thiazol-2-yl)ethyl}-2-(3-{[(3-iodophenyl)sulfonyl]amino}-6-methyl-2-oxohydropyridyl)acetamide;

N-{(1S)-1-[2-(Amidinoaminooxy)ethyl]-2-benzothiazol-2-yl-2-oxoethyl}-2-(3-{[(3-iodophenyl)sulfonyl]amino}-6-methyl-2-oxohydropyridyl) acetamide; and (2S)4-(Amidinoaminooxy)-2-[2-(3-{[(3-iodophenyl)sulfonyl]amino}-6-methyl-2-oxohydropyridyl)acetylamino]-N-methoxy-N-methylbutanamide; and pharmaceutically acceptable salts thereof.

30. A pharmaceutical composition, comprising a compound of claim 1, and a pharmaceutically acceptable carrier or diluent.

31. A method of treating pancreatitis, thrombosis, ischemic, stroke, restenosis, emphysema or inflammation in a mammal in need thereof, comprising administering to the mammal an effective amount of a composition of claim 30.

32. A method of inhibiting thrombin-induced platelet aggregation and clotting of fibrinogen in plasma in a mammal in need thereof, comprising administering to the mammal an effective amount of a composition of claim 30.

33. A method for inhibiting thrombin in blood comprising adding to the blood a compound of claim 1.

34. A method for inhibiting formation of blood platelet aggregates in blood comprising adding to the blood a compound of claim 1.

35. A method for inhibiting thrombus formation in blood comprising adding to the blood a compound of claim 1.

* * * * *

UNITED STATES PATENT AND TRADEMARK OFFICE
CERTIFICATE OF CORRECTION

PATENT NO. : 6,420,397 B1
DATED : July 16, 2002
INVENTOR(S) : Pan et al.

It is certified that error appears in the above-identified patent and that said Letters Patent is hereby corrected as shown below:

Column 44,
Line 64, change "$R^1$" to -- $R^f$ --.

Column 45,
Between lines 55 and 60, delete one occurrence of the following structure:

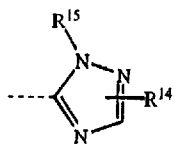

Column 46,
Lines 16-17, change "$C_{6-10}ar(C_{1-14})alkyl$" to -- $C_{6-10}ar(C_{1-4})alkyl$ --.
Line 26, change "di-$C_{14}$alkylamino($C_{2-6}$)alkoxy" to -- di-$C_{1-4}$alkylamino($C_{2-6}$) alkoxy --.
Line 42, change "amninobenzyl" to -- aminobenzyl --.

Column 47,
Line 66, change "claim 10" to -- claim 11 --.

Column 49,
Lines 28 and 29, change "3-chloro-2-cyanophenoxy)phenyl" to
-- 3-chloro-2-cyanophenoxyphenyl --.
Line 35, delete "benzyl".

Signed and Sealed this

Third Day of December, 2002

JAMES E. ROGAN
*Director of the United States Patent and Trademark Office*